US011065183B2

(12) United States Patent
Matsuo et al.

(10) Patent No.: US 11,065,183 B2
(45) Date of Patent: *Jul. 20, 2021

(54) CURABLE COMPOSITION

(71) Applicant: TOKUYAMA DENTAL CORPORATION, Tokyo (JP)

(72) Inventors: Takuma Matsuo, Tokyo (JP); Hironobu Akizumi, Tokyo (JP)

(73) Assignee: TOKUYAMA DENTAL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/605,602

(22) PCT Filed: Apr. 16, 2018

(86) PCT No.: PCT/JP2018/015735
§ 371 (c)(1),
(2) Date: Oct. 16, 2019

(87) PCT Pub. No.: WO2018/194032
PCT Pub. Date: Oct. 25, 2018

(65) Prior Publication Data
US 2020/0121564 A1    Apr. 23, 2020

(30) Foreign Application Priority Data

Apr. 18, 2017  (JP) .............. JP2017-082023
Sep. 4, 2017   (JP) .............. JP2017-169730

(51) Int. Cl.
| A61K 6/887 | (2020.01) |
| A61K 6/77  | (2020.01) |
| A61K 6/878 | (2020.01) |
| A61K 6/871 | (2020.01) |
| A61K 6/17  | (2020.01) |
| A61K 6/16  | (2020.01) |

(52) U.S. Cl.
CPC .............. *A61K 6/887* (2020.01); *A61K 6/17* (2020.01); *A61K 6/77* (2020.01); *A61K 6/871* (2020.01); *A61K 6/878* (2020.01); *A61K 6/16* (2020.01)

(58) Field of Classification Search
CPC .................................... A61K 6/17; A61K 6/16
See application file for complete search history.

(56) References Cited

U.S. PATENT DOCUMENTS

| 3,729,313 A    | 4/1973  | Smith             |
| 3,741,769 A    | 6/1973  | Smith             |
| 4,020,557 A    | 5/1977  | Rockett et al.    |
| 5,545,676 A    | 8/1996  | Palazzotto et al. |
| 2004/0180983 A1| 9/2004  | Hara et al.       |
| 2008/0319104 A1| 12/2008 | Klapdohr et al.   |
| 2011/0196062 A1| 8/2011  | Craig             |
| 2013/0096226 A1| 4/2013  | Toriyabe et al.   |
| 2013/0172441 A1| 7/2013  | Takahata et al.   |
| 2014/0206792 A1| 7/2014  | Ishizaka et al.   |
| 2014/0213687 A1| 7/2014  | Yamazaki et al.   |
| 2014/0295376 A1| 10/2014 | Uchida et al.     |
| 2015/0094396 A1| 4/2015  | Nakatsuka et al.  |
| 2015/0272833 A1| 10/2015 | Toriyabe et al.   |
| 2017/0049665 A1| 2/2017  | Kita et al.       |
| 2017/0196667 A1| 7/2017  | Teramae et al.    |
| 2018/0303721 A1| 10/2018 | Akizumi et al.    |
| 2019/0192386 A1| 6/2019  | Fukudome et al.   |

FOREIGN PATENT DOCUMENTS

| EP | 1236459 A1      | 9/2002  |
| EP | 2583660 A1      | 4/2013  |
| EP | 2902007 A1      | 8/2015  |
| EP | 3366269 A1      | 8/2018  |
| EP | 3536302 A1      | 9/2019  |
| JP | S62-086003 A    | 4/1987  |
| JP | S63-218703 A    | 9/1988  |
| JP | S63-273602 A    | 11/1988 |
| JP | 2001239661 A    | 9/2001  |
| JP | 2004276492 A    | 10/2004 |
| JP | 2005-089729 A   | 4/2005  |
| JP | 2006-117543 A   | 5/2006  |

(Continued)

OTHER PUBLICATIONS

H. Matsumura et al., "Adhesion Yearbook 2006," 1st Edition, Quintessence Publishing Ca, Ltd., Aug. 2006, pp. 129-137 (14 pages) with partial translation.

M. Miyazaki, "Science & Technique of Composite Resin Restoration," 1st Edition, Quintessence Publishing Co., Ltd., Jan. 2010, pp. 48-49 (6 pages) with partial translation.

International Search Report issued in corresponding International Application No. PCT/JP2018/015735; dated Jul. 24, 2018 (2 pages).

Written Opinion of the International Searching Authority issued in corresponding International Application No. PCT/JP2018/015735; dated Jul. 24, 2018 (5 pages).

Office Action issued in corresponding Brazilian Application No. BR1120190094563, dated Jul. 1, 2020 (47 pages).

Extended European Search Report issued in the European Application No. 178760443, dated Oct. 25, 2019 (13 pages).

(Continued)

*Primary Examiner* — Michael F Pepitone
(74) *Attorney, Agent, or Firm* — Osha Bergman Watanabe & Burton LLP

(57) ABSTRACT

Provided is a curable composition comprising a polymerizable monomer (A); spherical particles (B) having an average primary-particle diameter in a range of 230 nm to 1,000 nm; and a polymerization initiator (C), in which 90% or more of individual particles constituting the spherical particles (B) lies in a range of ±5% based on the average primary-particle diameter, and the refractive index of the spherical particles (B) is larger than the refractive index of a polymer of the polymerizable monomer (A). When a 1 mm-thick cured product is formed from the curable composition and the Y value (Yb) of the colored light of the cured product on a black background and the Y value (Yw) of the colored light of the cured product on a white background are each measured using a color difference meter, the ratio therebetween, Yb/Yw, being within a range of 0.2 to 0.5.

11 Claims, No Drawings

(56) References Cited

FOREIGN PATENT DOCUMENTS

| JP | 2007532518 A | 11/2007 |
|---|---|---|
| JP | 2012505823 A | 3/2012 |
| JP | 2012-087086 A | 5/2012 |
| JP | 2012153640 A | 8/2012 |
| JP | 2014-189503 A | 10/2014 |
| JP | 2015-067594 A | 4/2015 |
| JP | 2016-169180 A | 9/2016 |
| RU | 2472708 C2 | 1/2013 |
| WO | 2009/014031 A1 | 1/2009 |
| WO | 2011158742 A1 | 12/2011 |
| WO | 2012042911 A1 | 4/2012 |
| WO | 2012/176877 A1 | 12/2012 |
| WO | 2013039169 A1 | 3/2013 |
| WO | 2014050634 A1 | 4/2014 |
| WO | 2015-125470 A1 | 8/2015 |
| WO | 2017/069274 A1 | 4/2017 |
| WO | 2018/043595 A1 | 3/2018 |
| WO | 2018101236 A1 | 6/2018 |

OTHER PUBLICATIONS

International Search Report including Written Opinion issued in the International Application No. PCT/JP2017/042522 dated Jan. 23, 2018 (14 pages).
H. Shinoda et al., "Shikisai Kogaku Nyumon", Morikita Publishing Co., Ltd., 1st print published on May 1, 2007, pp. 73-78, with Partial English Translation (10 pages).
K. Saito, "Hikari to Shikisai no Kagaku", Kodansha, Ltd., 1st print published on Oct. 20, 2010, pp. 118-139, with Partial English Translation (21 pages).
The Color Science Association of Japan, ed., "Handbook of Color Science (3rd Edition)", University of Tokyo Press, published in Apr. 2011, pp. 1130-1181, with Partial English Translation (35 pages).
"Names of non-luminous object colours", JIS Z8102, revised Mar. 20, 2001, pp. 1-25, with Partial English Translation (16 pages).
"Colour specification-Names of light-source colours", JIS Z8110, revised Mar. 1, 1995, pp. 1-13, with Partial English Translation (9 pages).
H. Hosoda, "Basics of Photopolymerizable Composite Resins and Clinics", Nippon Shika Shuppan Co., Feb. 10, 1986, pp. 9-20, with Partial English Translation (9 pages).
T. Yamaoka, "Dictionary of Applied Optical Technologies and Materials", published by Industrial Technical Service Center Co., Ltd., Apr. 26, 2006, pp. 108-112, with Partial English Translation (4 pages).
Chemical Society of Japan, ed., "Chemistry Handbook, Fundamentals-II, Third Revision", published by Maruzen, Inc., Jun. 25, 1984, pp. 337-345 (5 pages).
International Search Report including Written Opinion issued in the International Application No. PCT/JP2018/008396, dated Apr. 17, 2018 (20 pages).
J. Yamagawa, "New Standard of Hybrid Arising from Pursuit of Lasting Aesthetics—Hybrid-type Hardness Region (pearl aesthetics)", Japanese Dental Technologists Association, 2011, No. 503, pp. 5-8 (6 pages).
International Search Report including Written Opinion issued in the International Application No. PCT/JP2018/015734 dated Jun. 12, 2018 (15 pages).
Office Action issued in the U.S. Appl. No. 16/465,018, dated Jul. 10, 2020 (10 pages).
Office Action issued in the U.S. Appl. No. 16/605,617, dated Jul. 10, 2020 (12 pages).
Extended European Search Report issued in the related European Application No. 18763621.2, dated Oct. 22, 2020 (10 pages).
Extended European Search Report issued in the European Application No. 18787662.8, dated Dec. 17, 2020 (6 pages).
Extended European Search Report issued in the related European Application No. EP18788652.8, dated Oct. 23, 2020 (8 pages).
Extended European Search Report issued in the related European Application No. 18788652.8, dated Oct. 23, 2020 (8 pages).
Office Action issued in the related Russian Patent Application No. 2019134976, dated Mar. 23, 2021 (11 pages).

CURABLE COMPOSITION

CROSS-REFERENCE TO RELATED APPLICATIONS:

This application claims priority to Japanese Patent Application No. 2017-082023 filed on Apr. 18, 2017, and to Japanese Patent Application No. 2017-169730 filed on Sep. 4, 2017. The disclosures of each of these priority applications are incorporated in their entirety in the present specification by reference.

TECHNICAL FIELD

The present invention relates to a curable composition that can have the external appearance color tone well-controlled without using a dye and a pigment, and exhibits reduced decoloration and discoloration. More particularly, the present invention relates to a curable composition useful as a dental curable composition for a dental filling restorative material that provides excellent convenience and esthetics.

BACKGROUND ART

Curable compositions including inorganic or organic fillers and polymerizable monomers have been conventionally used in a variety of fields such as construction materials, recording materials, and dental materials. Particularly, since dental filling restorative materials can impart color tones equivalent to the color tone of natural tooth color and are easily operable, dental filling restorative materials have been rapidly popularized as materials for restoring teeth that have been damaged by dental caries, fracture, and the like. In recent years, as a result of an enhancement of the mechanical strength and an enhancement of the adhesive force to teeth, dental filling restorative materials are also used for the restoration of anterior teeth as well as for molar teeth to which high occlusal pressure is exerted.

In recent years, in the field of dental filling restorative materials, there is an increasing demand not only for the recovery of occlusion but also for esthetic restoration of the appearance looking like natural teeth. There is a demand for a restorative material which can reproduce not only simple equivalent color tones but also the transparency and color tones at various restoration sites of teeth.

A natural tooth is formed from dentine and enamel, and the color tone (hue, chroma, and value) varies from site to site. For example, since an incisal part has a thin dentinal layer and is almost covered with enamel, the incisal part is highly transparent. In contrast, the tooth cervix is opaque because the dentinal layer is thick, and compared to an incisal part, the tooth cervix has high value (lightness or darkness of a color) and high chroma (vividness of color). That is, in a natural tooth, the chroma and value decrease in the direction from the tooth cervix where the dentinal layer is thick, toward the incisal part where the dentinal layer is thin. As such, since a tooth has different color tones at different sites, in order to obtain superior esthetic properties for tooth restoration, it is important to prepare a plurality of curable pastes having different color tones, and to select and use, from among those curable pastes, a curable paste having a color tone that is most suitable for the actual restored tooth and teeth adjacent thereto (hereinafter, also referred to as "periphery of the restored tooth") (see, for example, Non-Patent Document 1).

Such selection of color tone is carried out by a dentist, who uses a shade guide (color sample) that includes a collection of various cured product samples of prepared curable pastes, compares the respective color tones of the respective samples with the color tone of the periphery of the restored tooth that is checked by looking into the oral cavity, and selects a color tone that is felt to be closest to the color tone of the periphery of the restored tooth.

Furthermore, as long as it is not the case that the damage of the restored tooth is small with a shallow cavity, it is difficult to realize the adaptation of the color tone by means of filling of a single kind of curable paste. That is, if the cavity is deep (for example, Class 4 cavity), the color tone of a tooth is visually perceived in a state in which not only the color tone of the tooth flank part (enamel portion) but also the color tone of the deep part (dentinal portion) that shows through are combined to give a rich gradation. Therefore, a deep cavity is filled by laminating the curable pastes to be filled, by varying the color tone at a certain interval of depth, and thereby this subtle color tone is reproduced. Usually, this reproduction of color tone is carried out such that a plurality of curable pastes for dentinal restoration, which reproduce the color tones of the dentinal portion, is used and laminated from the deepest part (usually, lamination is continued while each layer is cured), and a curable paste for enamel restoration is laminated at the last surface layer (for example, see Non-Patent Documents 1 and 2).

As such, since there are individual differences and site differences in the color tone of teeth, arranging curable pastes that have their color tones strictly controlled in consideration of these differences, is substantially impossible in reality because a huge number of curable pastes are needed. Furthermore, efforts are needed to select curable pastes having the color tones of teeth from a plurality of thus prepared curable pastes having different color tones.

In addition, pigments, dyes, and the like have been conventionally used for the adjustment of the color tone of a curable composition such as a curable paste, and a variety of color tones have been prepared by changing the mixing proportions of pigments, dyes, and the like having different color tones. However, the coloration by such pigments and dyes tends to deteriorate over years, causing decoloration or discoloration. In dental filling restorative materials, a phenomenon has frequently occurred, in which the material exhibits high color tone adaptability immediately after restoration but undergoes discoloration with a lapse of time after the restoration, and the external appearance of the restored site does not match that of a natural tooth.

In this regard, as a technology of coloring without using pigments, dyes, and the like, utilization of light interference is known in the field of interior construction materials or the field of recording materials (see, for example, Patent Documents 1 and 2). Coloration achieved by utilizing light interference has an advantage that the phenomenon of decoloration or discoloration observed in the case of using a pigment, a dye, and the like does not occur.

Patent Document 1: Japanese Unexamined Patent Application, Publication No. 2004-276492
Patent Document 2: Japanese Unexamined Patent Application, Publication No. 2001-239661
Non-Patent Document 1: MATSUMURA, Hideo and TAGAMI, Junji, rev., "Adhesion Yearbook 2006", 1$^{st}$ Edition, Quintessence Publishing Co., Ltd., published in August, 2006, pp. 129-137

Non-Patent Document 2: MIYAZAKI, Masashi, "Science & Technique of Composite Resin Restoration", 1$^{st}$ Edition, Quintessence Publishing Co., Ltd., published in January, 2010, pp. 48-49

DISCLOSURE OF THE INVENTION

Problems to be Solved by the Invention

Restoration of teeth susing a curable composition that utilizes colored light brought by interference of light (hereinafter, also referred to as "interfering light") is advantageous because there is no phenomenon of decoloration or discoloration that is seen in the case of using a colorant substance such as a pigment. However, for this restoration, there is a problem that a plurality of curable compositions needs to be prepared in order to adapt to the color tone of a natural tooth having shades in accordance with individual differences or different sites of restoration, and that in a case in which the depth of the cavity to be restored is deep, a plurality of curable compositions having different color tones needs to be used for lamination.

Therefore, an object of the present invention is to provide a curable composition, with which it is not necessary to prepare a plurality of curable compositions having different color tones, a restoration resulting in an external appearance of a cured object to be formed that conforms to the color tone of a natural tooth is enabled, without laminating using a plurality of curable compositions having different color tones, and matching of the cured product to be formed with natural teeth is sustained; and a dental filling restorative material formed from the composition.

Means for Solving the Problems

In view of the above-described problems, the present inventors have conducted a thorough investigation. As a result, the inventors found that for a curable composition including spherical particles having a particular particle diameter, when the contrast ratio of the curable composition is controlled, the difference between the color tone of a filled portion and the color tone of a non-filled portion of a restoration product is small, the curable composition exhibits excellent color tone adaptability to natural teeth, and thus the above-described problems can be solved. Thus, the inventors completed the present invention.

That is, the curable composition of the present invention includes a polymerizable monomer (A), spherical particles (B) having an average primary-particle diameter in the range of 230 nm to 1,000 nm, and a polymerization initiator (C), in which 90% or more of the individual particles constituting the spherical particle (B) lie in the range of ±5% based on the average primary-particle diameter, the polymerizable monomer (A) and the spherical particles (B) satisfy requirement (X1) represented by the following formula (1):

$$nP < nF \qquad (1)$$

in formula (1), nP represents a refractive index at 25° C. of a polymer obtained by polymerizing the polymerizable monomer (A); and nF represents a refractive index at 25° C. of the spherical particles (B), and
when a 1 mm-thick cured product is formed from the curable composition and the Y value (Yb) of the colorimetric value according to the Munsell Color System of the colored light of the cured product on a black background and the Y value (Yw) of the colorimetric value according to the Munsell Color System of the colored light of the cured product on a white background are each measured using a color difference meter, the ratio therebetween, Yb/Yw, being within the range of 0.2 to 0.5.

Furthermore, the dental filling restorative material of the present invention is formed from the curable composition of the present invention.

Effects of the Invention

The curable composition of the present invention exhibits color development conforming to the color tones of natural teeth that vary depending on the individual differences or the sites of restoration, and therefore, it is not necessary to prepare a plurality of curable compositions having different color tones. Furthermore, when the curable composition of the present invention is used, a cured product can be formed conveniently without performing lamination using a plurality of curable compositions having different color tones, and restoration is enabled, in which the external appearance of a cured product to be formed conforms to the color tone of a natural tooth, irrespective of the depth of the cavity. Furthermore, since the curable composition of the present invention utilizes interfering light, decoloration and discoloration does not occur, and restoration by which matching of a cured product to be formed and natural teeth is sustained, is enabled. Therefore, the curable composition of the present invention can be suitably used as a dental curable composition, particularly as a dental filling restorative material.

PREFERRED MODE FOR CARRYING OUT THE INVENTION

The curable composition of the present invention includes a polymerizable monomer (A), spherical particles (B) having an average primary-particle diameter in the range of 230 nm to 1,000 nm, and a polymerization initiator (C).

In order to achieve convenience of the operability for restoration of a cavity and sustainment of excellent esthetics and matching with natural teeth having a wide variety of color tones, the most significant feature of the present invention is that spherical particles (B) having a narrow particle size distribution are used, as well as that the polymerizable monomer (A) and the spherical particles (B) are selected such that the relationship between the refractive index of the polymerizable monomer (A) and the refractive index of the spherical particles (B) satisfies requirement (X1) represented by the following formula (1):

$$nP < nF \qquad (1)$$

in which nP represents the refractive index at 25° C. of a polymer obtained by polymerizing the polymerizable monomer (A); and nF represents the refractive index at 25° C. of the spherical particles (B)), and
when a cured product having a thickness of 1 mm is formed, and the Y value (Yb) of the colorimetric value according to the Munsell Color System of the colored light of the cured product on a black background (backing having a value of 1 according to the Munsell Color System) and the Y value (Yw) of the colorimetric value according to the Munsell Color System of the colored light of the cured product on a white background (backing having a value of 9.5 according to the Munsell Color System) are each measured using a color difference meter, the ratio (Yb/Yw) satisfies the range of 0.2 to 0.5. Hereinafter, this ratio (Yb/Yw) is also referred to as contrast ratio.

As the conditions described above are all satisfied, a curable composition, particularly a curable composition that can be used as a dental filling restorative material, with which colored light induced by interference of light can be clearly identified even without using a dye, a pigment, and the like, and restoration with satisfactory color tone adaptability close to natural teeth is enabled irrespective of the depth of the cavity, can be obtained. Meanwhile, it is thought that the relationship between the particle diameter of the spherical particles (B) and the phenomenon of light interference conforms to the Bragg's diffraction condition.

There are individual differences in the color tone of natural teeth, and the color tone may vary depending on the site to be restored; however, the curable composition of the present invention that utilizes the phenomenon of light interference can cope with various color tones. Specifically, in a case in which the chromaticity (hue and chroma) of a foundation tooth is high, external light such as radiated light is absorbed by a background having high chromaticity, and light other than the colored light (interfering light) produced from the curable composition that utilizes the phenomenon of light interference is suppressed. Therefore, a colored light can be observed. On the other hand, in a case in which the chromaticity of the foundation tooth is low, since external light such as radiated light is scattered and reflected by a background having low chromaticity, and the scattered and reflected light is stronger than the colored light (interfering light) produced from the curable composition that utilizes the phenomenon of light interference, the colored light is canceled and becomes weak.

Therefore, since strong colored light is produced in a natural tooth having high chromaticity, and weak colored light is produced in a natural tooth having low chromaticity, wide color tone adaptability can be exhibited with one kind of paste. As such, it is difficult to achieve the technology of matching the color tone of a natural tooth using one kind of paste irrespective of the level of chromaticity, in the case of a paste that is produced by mixing of coloring substances such as pigments.

The curable composition of the present invention has a feature that a colored light is produced by an interference phenomenon. Whether this colored light is produced or not is verified by measuring the spectral reflectance characteristics using a color difference meter under the conditions of making measurement on both a black background and a white background. On a black background, in a case in which the above-mentioned conditions are satisfied, a characteristic reflection spectrum corresponding to the colored light is clearly identified; however, on a white background, a substantially uniform reflectance is exhibited over substantially the entire range of the visible spectrum (380 nm to 780 nm), and a particular reflection visible spectrum is not identifiable, while the light is substantially colorless. This is speculated to be because, on a black background, external light (for example, C light source or D65 light source) is absorbed or blocked, and a colored light induced by interference is emphasized; whereas on a white background, since scattered and reflected light of external light is strong, a colored light induced by interference is not easily observed.

In order to exhibit the effect of the present invention of having excellent color tone adaptability, it is important that the relationship between the refractive index nP at 25° C. of a polymer of the polymerizable monomer (A) and the refractive index nF at 25° C. of the spherical particles (B) is established so as to satisfy the following formula (1), and the contrast ratio (Yb/Yw) of a cured product of the curable composition is adjusted in the range of 0.2 to 0.5.

$$nP<nF \qquad (1)$$

As shown in formula (1), the curable composition of the present invention is such that the relationship between the refractive index nP at 25° C. of a polymer of the polymerizable monomer (A) and the refractive index nF at 25° C. of the spherical particles (B) is nP<nF. In a case in which the refractive index nF of the spherical particles (B) is high, and the refractive index nP of a polymer of the polymerizable monomer (A) is low, interfering light conforming to the Bragg's diffraction conditions is exhibited. However, in an opposite case, light having a short wavelength is more easily subjected to interference, and a colored light thus obtainable has a shorter wavelength and acquires a bluish tint. Thus, in a cavity of a natural tooth formed over from the enamel to the dentine, the color tone adaptability to the tooth is likely to become defective.

Furthermore, in a case in which the contrast ratio (Yb/Yw) of a cured product of the curable composition according to the present invention is less than 0.2, the value (lightness and darkness of color) of the cured product at a site of filling becomes low, the transmitted light becomes strong at the site of filling, while the colored light from the cured product becomes weak. Therefore, it is considered that in a case in which a deep cavity (for example, Class 4 cavity) is filled with the cured product, the color tone adaptability as an effect of the present invention cannot be easily obtained. Meanwhile, in a case in which the contrast ratio (Yb/Yw) of the cured product is more than 0.5, the value of the cured product becomes high, and light cannot easily penetrate into the restoration product that becomes the foundation. Therefore, the reflected light at the surface of the site of filling becomes strong, and the colored light coming from the cured product becomes weak. Thus, it is considered that the color tone adaptability as an effect of the present invention cannot be easily obtained.

In order to have excellent color tone adaptability irrespective of the depth of the cavity, the contrast ratio (Yb/Yw) of the cured product of the curable composition is in the range of 0.2 to 0.5, preferably in the range of 0.20 to 0.47, and more preferably in the range of 0.20 to 0.45.

Meanwhile, the contrast ratio (Yb/Yw) of a cured product of the curable composition can be adjusted by means of, for example, the difference between the refractive index of a polymer of the polymerizable monomer (A) and the refractive index of the spherical particles (B), the particle diameter of the spherical particles (B), the percentage content of the inorganic particles (D) that will be described below, and the like. Specifically, when the difference between the refractive index of a polymer of the polymerizable monomer (A) and the refractive index of the spherical particles (B) becomes large, the contrast ratio (Yb/Yw) tends to increase, and when the difference between the refractive index of the polymer of the polymerizable monomer (A) and the refractive index of the spherical particles (B) becomes small, the contrast ratio (Yb/Yw) tends to decrease. Furthermore, when the average primary-particle diameter of the spherical particles (B) becomes large, the contrast ratio (Yb/Yw) tends to increase, and when the average primary-particle diameter of the spherical particles (B) becomes small, the contrast ratio (Yb/Yw) tends to decrease. Furthermore, when the percentage content of the inorganic particles (D) becomes large, the contrast ratio (Yb/Yw) tends to increase, and when the percentage content of the inorganic particles (D) becomes small, the contrast ratio (Yb/Yw) tends to decrease.

When the curable composition of the present invention is used, for example, when measurement is made using a two-dimensional colorimeter in the class of A system (red-brown) according to a shade guide ("VITA Classical", manufactured by Vita Zahnfabrik H. Rauter GmbH & Co. KG) in a state in which the curable composition is filled into cavities of restoration products having a depth of 1 mm and 5 mm and cured, the color difference (ΔE*) between the colorimetric values of a filled portion and a non-filled portion can be adjusted to be 3.5 or less. Furthermore, when measurement is made using a two-dimensional colorimeter in the class of B system (red-yellow) according to a shade guide ("VITA Classical", manufactured by Vita Zahnfabrik H. Rauter GmbH & Co. KG) in a state in which the curable composition is filled into cavities of restoration products having a depth of 1 mm and 5 mm and cured, the color difference (ΔE*) between the colorimetric values of a filled portion and a non-filled portion can be adjusted to be 3.5 or less. That is, the curable composition of the present invention has excellent color tone adaptability even though the color tone of teeth and the depth of cavities are different.

Hereinafter, various components of the curable composition of the present invention will be described.

<Polymerizable Monomer (A)>

Regarding the polymerizable monomer (A), any known polymerizable monomer can be used without any particular limitations. From the viewpoint of the polymerization rate, a radical polymerizable or cationic polymerizable monomer is preferred. A particularly preferred radical polymerizable monomer is a (meth)acrylic compound, and examples of the (meth)acrylic compound include (meth)acrylates listed below. Furthermore, particularly preferred examples of the cationic polymerizable monomer include epoxies and oxetanes.

Generally, examples of (meth)acrylates as the (meth)acrylic compounds that are suitably used, include compounds shown in the following (I) to (IV).

(I) Monofunctional Polymerizable Monomer (I-i) Compound that does not have Acidic Group and Hydroxy Group methyl (meth) acrylate,
ethyl (meth) acrylate,
n-butyl (meth) acrylate,
2-ethylhexyl (meth) acrylate,
n-lauryl (meth) acrylate,
n-stearyl (meth) acrylate,
tetrafurfuryl (meth) acrylate,
glycidyl (meth) acrylate,
methoxyethylene glycol (meth) acrylate,
methoxydiethylene glycol (meth) acrylate,
methoxytriethylene glycol (meth) acrylate,
methoxypolyethylene glycol (meth) acrylate,
ethoxyethylene glycol (meth) acrylate,
ethoxydiethylene glycol (meth) acrylate,
ethoxytriethylene glycol (meth) acrylate,
ethoxypolyethylene glycol (meth) acrylate,
phenoxyethylene glycol (meth) acrylate,
phenoxydiethylene glycol (meth) acrylate,
phenoxytriethylene glycol (meth) acrylate,
phenoxypolyethylene glycol (meth) acrylate,
cyclohexyl (meth) acrylate,
benzyl (meth) acrylate,
isobornyl (meth) acrylate,
trifluoroethyl (meth)acrylate, and the like.

(I-ii) Compound Having Acidic Group (meth)acrylic acid,
N-(meth)acryloyl glycine,
N-(meth)acryloyl aspartic acid,
N-(meth)acryloyl-5-aminosalicylic acid,
2-(meth)acryloyloxyethyl hydrogen succinate,
2-(meth)acryloyloxyethyl hydrogen phthalate,
2-(meth)acryloyloxyethyl hydrogen malate,
6-(meth)acryloyloxyethyl naphthalene-1,2,6-tricarboxylic acid,
0-(meth)acryloyl tyrosine,
N-(meth)acryloyl tyrosine,
N-(meth)acryloyl phenylalanine,
N-(meth)acryloyl-p-aminobenzoic acid,
N-(meth)acryloyl-o-aminobenzoic acid,
p-vinylbenzoic acid,
2-(meth)acryloyloxybenzoic acid,
3-(meth)acryloyloxybenzoic acid,
4-(meth)acryloyloxybenzoic acid,
N-(meth)acryloyl-5-aminosalicylic acid,
N-(meth)acryloyl-4-aminosailcylic acid, and the like,
and compounds obtained by converting carboxyl groups of these compounds to acid anhydride groups;
11-(meth)acryloyloxyundecane-1,1-dicarboxylic acid,
10-(meth)acryloyloxydecane-1,1-dicarboxylic acid,
12-(meth)acryloyloxydodecane-1,1-dicarboxylic acid,
6-(meth)acryloyloxyhexane-1,1-dicarboxylic acid,
2-(meth)acryloyloxyethyl-3'-methacryloyloxy-2'-(3,4-dicarboxybenzoyloxy)propyl succinate,
4-(2-(meth)acryloyloxyethyl) trimellitate anhydride,
4-(2-(meth)acryloyloxyethyl) trimellitate,
4-(meth)acryloyloxyethyl trimellitate,
4-(meth)acryloyloxybutyl trimellitate,
4-(meth)acryloyloxyhexyl trimellitate,
4-(meth)acryloyloxydecyl trimellitate,
4-(meth)acryloyloxybutyl trimellitate,
6-(meth)acryloyloxyethyl naphthalene-1,2,6-tricarboxylic acid anhydride,
6-(meth)acryloyloxyethyl naphthalene-2,3,6-tricarboxylic acid anhydride,
4-(meth)acryloyloxyethylcarbonylpropionoyl-1,8-naphthalic anhydride,
4-(meth)acryloyloxyethylnaphthalene-1,8-tricarboxylic acid anhydride,
9-(meth)acryloyloxynonane-1,1-dicarboxylic acid,
13-(meth)acryloyloxytridecane-1,1-dicarboxylic acid,
11-(meth)acrylamidoundecane-1,1-dicarboxylic acid,
2-(meth)acryloyloxyethyl dihydrogen phosphate,
2-(meth)acryloyloxyethylphenyl hydrogen phosphate,
10-(meth)acryloyloxydecyl dihydrogen phosphate,
6-(meth)acryloyloxyhexyl dihydrogen phosphate,
2-(meth)acryloyloxyethyl-2-bromoethyl hydrogen phosphate,
2-(meth)acrylamidoethyl dihydrogen phosphate,
2-(meth)acrylamido-2-methylpropanesulfonic acid,
10-sulfodecyl (meth) acrylate,
3-(meth)acryloxypropyl-3-phosphonopropionate,
3-(meth)acryloxypropyl phosphonoacetate,
4-(meth)acryloxybutyl-3-phosphonopropionate,
4-(meth)acryloxybutyl phosphonoacetate,
5-(meth)acryloxypentyl-3-phosphonopropionate,
5-(meth)acryloxypentyl phosphonoacetate,
6-(meth)acryloxyhexyl-3-phosphonopropionate,
6-(meth)acryloxyhexyl phosphonoacetate,
10-(meth)acryloxydecyl-3-phosphonopropionate,
10-(meth)acryloxydecyl phosphonoacetate,
2-(meth)acryloxyethyl-phenyl phosphonate,
2-(meth)acryloyloxyethylphosphonic acid,
10-(meth)acryloyloxydecylphosphonic acid,
N-(meth)acryloyl-ω-aminopropylphosphonic acid,
2-(meth)acryloyloxyethylphenyl hydrogen phosphate, 2-(meth)acryloyloxyethyl-2'-bromoethyl hydrogen phosphate,
2-(meth)acryloyloxyethylphenyl phosphonate, and the like.
(I-iii) Compound Having Hydroxy Group
2-hydroxyethyl (meth) acrylate,
3-hydroxypropyl (meth) acrylate,
4-hydroxybutyl (meth) acrylate,
6-hydroxyhexyl (meth) acrylate,
10-hydroxydecyl (meth) acrylate,
propylene glycol mono(meth)acrylate,
glycerol mono(meth)acrylate,
erythritol mono(meth)acrylate,
N-methylol (meth) acrylamide,
N-hydroxyethyl (meth) acrylamide,
N,N-(dihydroxyethyl) (meth)acrylamide, and the like.
(II) Bifunctional Polymerizable Monomer
(II-i) Aromatic Compound-Based Monomer
2,2-bis(methacryloyloxyphenyl)propane,
2,2-bis[(3-methacryloyloxy-2-hydroxypropyloxy)phenyl] propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2(4-methacryloyloxydiethoxyphenyl)-2-(4-methacryloyloxytriethoxyphenyl)propane,
2(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl)propane, and the like,
and acrylates corresponding to these methacrylates;
diadducts obtainable from addition of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds having an aromatic group, such as methylbenzene diisocyanate and 4,4'-diphenylmethane diisocyanate; di(methacryloxyethyl)diphenylmethanediurethane, and the like.
(II-ii) Aliphatic Compound-Based Monomer
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate, and the like,
and acrylates corresponding to these methacrylates; diadducts obtainable from addition products of vinyl monomers having an —OH group, including methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds such as hexamethylene diisocyanate, trimethylhexamethylene diisocyanate, methylcyclohexane diisocyanate, isophorone diisocyanate, and methylenebis(4-cyclohexyl isocyanate), for example, 1,6-bis(methacrylethyloxycarbonylamino)trimethylhexane; 1,2-bis(3-methacryloyloxy-2-hydroxypropoxy)ethyl, and the like.

(III) Trifunctional polymerizable monomer
trimethylolpropane trimethacrylate,
trimethylolethane trimethacrylate,
pentaerythritol trimethacrylate,
trimethylolmethane trimethacrylate, and the like,
and acrylates corresponding to these methacrylates, and the like.
(IV) Tetrafunctional Polymerizable Monomer
pentaerythritol tetramethacrylate,
pentaerythritol tetraacrylate;
diadducts obtainable from addition products of diisocyanate compounds such as methylbenzene diisocyanate, methylcyclohexane diisocyanate, isophorone diisocyanate, hexamethylene diisocyanate, trimethylhexamethylene diisocyanate, methylenebis(4-cyclohexyl isocyanate), 4,4-diphenylmethane diisocyanate, and tolylene-2,4-diisocyanate, and glycidol dimethacrylate, and the like.

Regarding these (meth)acrylate-based polymerizable monomers, a plurality of kinds of compounds may be used in combination, if necessary.

Furthermore, if necessary, a polymerizable monomer other than the above-described (meth)acrylate-based polymerizable monomers may also be used.

According to the present invention, as the polymerizable monomer (A), generally, a plurality of polymerizable monomers is used for the purpose of regulating the physical properties (mechanical characteristics and adhesiveness to the tooth substance in dental use applications) of a cured product of the curable composition. At that time, it is desirable that the types and amounts of the polymerizable monomers are set such that the refractive index of the polymerizable monomer (A) at 25° C. falls in the range of 1.38 to 1.55, from the viewpoint of the difference between the refractive index of the polymerizable monomer and the refractive index of the spherical particles (B) that will be described below. That is, in a case in which a silica-titanium group element oxide-based composite oxide, which enables easy adjustment of the refractive index, is used as the spherical particles (B), the refractive index nF of the spherical particles is in the range of about 1.45 to 1.58 depending on the content of the silica portion, and by setting the refractive index of the polymerizable monomer (A) to be in the range of 1.38 to 1.55, the refractive index nP of the polymer obtainable from the polymerizable monomer (A) can be set to be approximately in the range of 1.40 to 1.57. Thus, it is easy to satisfy formula (1). Meanwhile, in the case of using a plurality of kinds of polymerizable monomers as the polymerizable monomer (A), it is desirable that the refractive index of a mixture obtained by mixing the plurality of kinds of polymerizable monomers is in the above-mentioned range, and the individual polymerizable monomers may not necessarily have their refractive indices in the above-described range.

Meanwhile, the refractive index of polymerizable monomer or a cured product of the polymerizable monomer can be determined using an Abbe refractometer at 25° C.

<Spherical Particles (B)>

The dental filling restorative material contains various filler materials such as inorganic powders and organic powders; however, the curable composition of the present invention includes spherical particles (B) having an average primary-particle diameter in the range of 230 nm to 1,000 nm, for the purpose of expressing a colored light induced by interference. A feature of the curable composition of the present invention is that the constituent filler material is spherical in shape and has a narrow particle diameter distribution. A colored light induced by interference is produced at an area where constituent particles are regularly accumulated. The spherical particles (B) that constitute the curable composition of the present invention have a uniformly spherical shape and have a narrow particle diameter distribution, and therefore, a colored light induced by interference is produced. In contrast, when irregularly shaped particles that are produced by pulverization or the like are used, the shape is also non-uniform, and the particle diameter distribution is broad. Therefore, the particles are not regularly accumulated, and a colored light induced by interference is not produced.

As described above, for the spherical particles (B), it is important that the average primary-particle diameter of the particles is 230 nm to 1,000 nm, and at least 90% (number of particles) of the individual particles constituting the spherical particles (B) lie in the range of ±5% based on the average primary-particle diameter. That is, the spherical particles (B) are composed of a plurality of primary particles, and primary particles in a number of 90% or more among the entire primary particles are present in the range of ±5% based on the average particle diameter of the plurality of primary particles. Exhibition of a colored light induced by interference is achieved as diffraction and interference occur according to the Bragg's condition, and light having a particular wavelength is emphasized. Thus, when particles having the above-mentioned particle diameter are incorporated, a cured product of the curable composition exhibits a yellow to reddish colored light depending on the particle diameter. From the viewpoint of further enhancing the effect of exhibiting a colored light induced by interference, the average primary-particle diameter of the spherical particles (B) is suitably 230 nm to 800 nm, more suitably 240 nm to 500 nm, and even more suitably 260 nm to 350 nm. In a case in which spherical particles having an average primary-particle diameter in the range of 150 nm or greater and less than 230 nm are used, the colored light thus obtainable is bluish, and in a cavity of a natural tooth formed over from the enamel to the dentine, the color tone adaptability to the tooth substance is likely to be poor. Furthermore, in a case in which spherical particles having an average primary-particle diameter of less than 100 nm are used, the phenomenon of interference by visible light is not likely to occur. On the other hand, in a case in which spherical particles having an average primary-particle diameter of larger than 1,000 nm are used, exhibition of the phenomenon of light interference can be expected; however, in a case in which the curable composition of the present invention is used as a dental filling restorative material, problems such as sedimentation of the spherical particles and deterioration of abradability occur, which is not preferable.

The curable composition of the present invention exhibits various colored lights on a black background depending on the particle diameter of the spherical particles (B). Therefore, in order to obtain light having a desired color, the average primary-particle diameter of the spherical particles (B) may be decided to be in the range of 230 nm to 1,000 nm. In a case in which spherical particles having an average primary-particle diameter in the range of 230 nm to 260 nm are used, the colored light thus obtainable is yellowish, and the curable composition is useful for the restoration of teeth having a color in the class of B system (red-yellow) according to a shade guide ("VITA Classical", manufactured by Vita Zahnfabrik H. Rauter GmbH & Co. KG) and is particularly useful for the restoration of a cavity formed over from the enamel to the dentine. In a case in which spherical particles having an average primary-particle diameter in the range of 260 nm to 350 nm are used, the colored light thus obtainable is reddish, and the curable composition is useful for the restoration of teeth having a color in the class of A system (red-brown) according to a shade guide "VITA Classical", manufactured by Vita Zahnfabrik H. Rauter GmbH & Co. KG) and is particularly useful for the restoration of a cavity formed over from the enamel to the dentine. Since the hue of the dentine is reddish as such in many cases, an embodiment of using spherical particles having an average primary-particle diameter in the range of 260 nm to 350 nm is most preferable because adaptability to restored teeth having a variety of color tones is improved to a large extent. On the other hand, in a case in which spherical particles having an average primary-particle diameter in the range of 150 nm or greater and less than 230 nm are used, the colored light thus obtainable is bluish, and the color tone adaptability to the tooth substance is likely to be poor in a cavity formed over from the enamel to the dentine, as described above. However, the curable composition is useful for the restoration of the enamel and is particularly useful for the restoration of an incisal part.

It is important that the spherical particles (B) have an average primary-particle diameter in the above-described particle diameter range.

In an environment in which the periphery of a cured product of the curable composition of the present invention shows a reddish color, even if the environment changes variously from red-yellow color to red-brown color, all of the value, chroma, and hue match satisfactorily. Specifically, in a case in which the chromaticity (hue and chroma) of the background (backing environment) is high, external light such as radiated light is absorbed by the background having high chromaticity, and light other than the colored light from the cured product is suppressed. Therefore, colored light can be observed. On the other hand, in a case in which the chromaticity of the background (backing environment) is low, external light such as radiated light is scattered at the background having low chromaticity, and since the scattered light is stronger than the colored light from the cured product, the colored light is canceled and becomes weak. Therefore, in a backing environment having high chromaticity, strong colored light is produced, and in a backing environment having low chromaticity, weak colored light is produced. Accordingly, an effect of matching a variety of reddish peripheral environments to a large extent is exhibited.

According to the present invention, the average primary-particle diameters of the spherical particles (B) and the spherical inorganic filler (b2) that will be described below refer to the average values obtained by taking a photograph of the powder with a scanning electron microscope, selecting 30 or more particles observed within a unit viewing field of the photograph, and determining the respective primary-particle diameters (maximum diameters).

Furthermore, according to the present invention, the spherical shape may be approximately spherical, and it is not necessarily essential to be a perfect true sphere. When a photograph of particles is taken by scanning electron microscopy, the maximum diameter for each of the particles (thirty or more particles) present within a unit viewing field of the photograph is measured, and the average uniformity is obtained by dividing the particle diameter in a direction orthogonally intersecting the maximum diameter by the maximum diameter, the average uniformity is desirably 0.6 or higher, and more preferably 0.8 or higher.

In regard to the curable composition of the present invention, the spherical particles (B) may be included in any form as long as the above-mentioned conditions are satisfied. For example, the spherical particles (B) may be incorporated into the curable composition of the present invention as received as a powder. Furthermore, the spherical particles (B) may also be incorporated into the curable composition of the present invention as an organic-inorganic composite filler that is prepared by mixing the spherical particles (B) or aggregates obtained by aggregating the spherical particles (B) with a polymerizable monomer, polymerizing and curing the mixture, and then pulverizing the cured product. Alternatively, the spherical particles (B) as a powder and an organic-inorganic composite filler may be used in combination.

In the case of using the spherical particles (B) as a powder and an organic-inorganic composite filler, the spherical particles (B) as a powder and the spherical particles (B) in the organic-inorganic composite filler may be identical with each other, or may be different spherical particles.

Regarding the spherical particles (B), any spherical particles that are used as a component of a curable composition can be used without limitations. Specific examples include inorganic powders such as amorphous silica, silica-titanium group element oxide-based composite oxide particles (silica-zirconia, silica-titania, or the like), quartz, alumina, barium glass, strontium glass, lanthanum glass, fluoroaluminosilicate glass, ytterbium fluoride, zirconia, titania, and colloidal silica.

Among these, from the viewpoint that the adjustment of the refractive index of the filler is easy, silica-titanium group element oxide-based composite oxide particles are preferred.

The silica-titanium group element oxide-based composite oxide particles according to the present invention are composite oxides of silica and titanium group element (elements of Group 4 in the Periodic Table of Elements) oxides, and examples include silica-titania, silica-zirconia, and silica-titania-zirconia. Among these, from the viewpoint that the refractive index of the filler can be adjusted and high opacity to X-rays can be imparted, silica-zirconia is preferred. The composite ratio is not particularly limited; however, from the viewpoint of imparting sufficient opacity to X-rays and adjusting the refractive index to the suitable range that will be described below, it is preferable that the content of silica is 70 mol % to 95 mol %, and the content of the titanium group element oxide is 5 mol % to 30 mol %. In the case of silica-zirconia, the refractive index can be freely changed by changing the respective composite ratios as such.

Meanwhile, in these silica-titanium group element oxide-based composite oxide particles, compounding of a metal oxide other than silica and a titanium group element oxide is also allowed, as long as the amount is small. Specifically, an alkali metal oxide such as sodium oxide or lithium oxide may also be incorporated in an amount of 10 mol % or less.

The method for producing the silica-titanium group element oxide-based composite oxide particles is not particularly limited; however, in order to obtain the specific spherical particle of the present invention, for example, a so-called sol-gel method of adding a mixed solution including a hydrolyzable organosilicon compound and a hydrolyzable organotitanium group metal compound to an alkaline solvent, performing hydrolysis, and precipitating a reaction product, is suitably employed.

These silica-titanium group element oxide-based composite oxide particles may be surface-treated with a silane coupling agent. Through a surface treatment using a silane coupling agent, when the composite oxide particles are produced into an organic-inorganic composite filler, excellent interfacial strength between the composite filler and the organic resin matrix (b1) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be decided after the mechanical properties and the like of a cured product of the curable composition thus obtainable are checked in advance by experiments. An example of a suitable range is the range of 0.1 parts by mass to 15 parts by mass with respect to 100 parts by mass of the spherical particles (B).

As described above, a colored light induced by interference, scattering, or the like, which exhibits satisfactory color tone adaptability to natural teeth, is obtained in a case in which requirement (X1) represented by the following formula (1) is satisfied:

$$nP < nF \qquad (1)$$

in formula (1), nP represents the refractive index at 25° C. of a polymer obtainable by polymerizing the polymerizable monomer (A); and nF represents the refractive index at 25° C. of the spherical particles (B).

That is, the refractive index of the spherical particles (B) is in a state of being higher than the refractive index of a polymer obtained by polymerizing the polymerizable monomer (A). The difference between the refractive index nF (25° C.) of the spherical particles (B) and the refractive index nP (25° C.) of a polymer of the polymerizable monomer (A) is preferably 0.001 or more, more preferably 0.002 or more, and even more preferably 0.005 or more.

Furthermore, in a case in which the contrast ratio (Yb/Yw) of a cured product of the curable composition of the present invention is in the range of 0.2 to 0.5 as described above, from the viewpoint that a colored light induced by interference is vividly exhibited, and the color tone adaptability is enhanced, it is preferable that the refractive index difference between the refractive index nF of the spherical particles (B) and the refractive index nP of a polymer of the polymerizable monomer (A) is set to be 0.1 or less, and more preferably 0.05 or less, so that transparency is not impaired as far as possible.

The incorporation amount of the spherical particles (B) according to the present invention is preferably 10 parts by mass to 1,500 parts by mass with respect to 100 parts by mass of the polymerizable monomer (A). By incorporating 10 parts by mass or more of the spherical particles (B), colored light induced by interference, scattering, and the like is satisfactorily exhibited. Furthermore, in the case of using spherical particles for which the refractive index difference between the spherical particles and a polymer of the polymerizable monomer (A) is more than 0.1 are used as the spherical particles (B), there is a risk that the transparency of the cured product may be decreased, and the effect of exhibiting colored light may not be sufficiently exhibited. In consideration of these, the incorporation amount of the spherical particles (B) is more preferably 50 parts by mass to 1,500 parts by mass, and even more preferably 100 parts by mass to 1,500 parts by mass, with respect to 100 parts by mass of the polymerizable monomer (A).

In the spherical particles (B), the refractive index of the silica-titanium group element oxide-based composite oxide, for which the adjustment of the refractive index is easy, is in the range of about 1.45 to 1.58 according to the content of the silica portion. In the case of using the silica-titanium group element oxide-based composite oxide as the spherical particles (B), the refractive index nP of a polymer obtained from the polymerizable monomer (A) can be approximately set to the range of 1.40 to 1.57 by having the refractive index of the polymerizable monomer (A) set to the above-mentioned range (in the range of 1.38 to 1.55). Therefore, the spherical particles (B) can be easily selected so as to satisfy the above-mentioned condition (formula (1)). That is, a silica-titanium group element oxide-based composite oxide (for example, silica-titania or silica-zirconia) containing an adequate amount of silica portion may be used.

<Organic-Inorganic Composite Filler>

In the case of using the spherical particles (B) in the form of an organic-inorganic composite filler, the organic resin matrix included in the organic-inorganic composite filler is referred to as organic resin matrix (b1), and the spherical particle (B) is referred to as spherical inorganic filler (b2).

In a case in which the spherical particles (B) are used in the form of an organic-inorganic composite filler, when the difference between the refractive indices of the spherical inorganic filler (b2) and the organic resin matrix (b1), which constitute the organic-inorganic composite filler, and the difference between the refractive indices of the spherical inorganic filler (b2) and a polymer of the polymerizable monomer (A) are adjusted so as to satisfy the formulae (2) and (3) that will be described below, light diffraction and interference according to the Bragg's diffraction conditions occur even in a case in which an organic-inorganic composite filler is added to the curable composition. Thus, when the average primary-particle diameter of the spherical inorganic filler (b2) is the same as that of the spherical particles (B), a colored light having the same wavelength as in the case of using the spherical particles (B) alone is exhibited.

The spherical inorganic filler (b2) that constitutes the organic-inorganic composite filler may be identical to or different from the spherical particles (B) that are used as a powder; however, similarly to the spherical particles (B) used as a powder, the spherical inorganic filler (b2) is spherical in shape, has an average primary-particle diameter in the range of 230 nm to 1,000 nm, and 90% or more of individual particles constituting the spherical inorganic filler (b2) lies in the range of ±5% based on the average primary-particle diameter. Furthermore, it is important to satisfy the relationship between the refractive index $nM_{b1}$ of the organic resin matrix (b1) and the refractive index $nF_{b2}$ of the spherical inorganic filler (b2) as represented by the following formula (2), and the relationship between the refractive index nP of a polymer of the polymerizable monomer (A) and the refractive index $nF_{b2}$ of the spherical inorganic filler (b2) as represented by the following formula (3).

$$nM_{b1} < nF_{b2} \quad (2)$$

In formula (2), $nM_{b1}$ represents the refractive index at 25° C. of the organic resin matrix (b1) that constitutes the organic-inorganic composite filler; and $nF_{b2}$ represents the refractive index at 25° C. of the spherical inorganic filler (b2).

$$nP < nF_{b2} \quad (3)$$

In formula (3), nP represents the refractive index at 25° C. of a polymer of the polymerizable monomer (A); and $nF_{b2}$ represents the refractive index at 25° C. of the spherical inorganic filler (b2) that constitutes the organic-inorganic composite filler.

Thereby, even in a case in which the spherical particles (B) are used in the form of an organic-inorganic composite filler, a curable composition that can be used as a dental filling restorative material, particularly as a dental filling restorative material having satisfactory color tone adaptability, with which a colored light induced by light interference can be clearly identified even without using a dye, a pigment, or the like, and restoration close to natural teeth is enabled, can be obtained.

As described above, colored light induced by interference is exhibited with satisfactory color tone adaptability to natural teeth in a case in which the following formulae (2) and (3) are satisfied.

$$nM_{b1} < nF_{b2} \quad (2)$$

In formula (2), $nM_{b1}$ represents the refractive index at 25° C. of the organic resin matrix (b1) that constitutes the organic-inorganic composite filler; and $nF_{b2}$ represents the refractive index at 25° C. of the spherical inorganic filler (b2).

$$nP < nF_{b2} \quad (3)$$

In formula (3), nP represents the refractive index at 25° C. of a polymer of the polymerizable monomer (A); and $nF_{b2}$ represents the refractive index at 25° C. of the spherical inorganic filler (b2) that constitutes the organic-inorganic composite filler.

That is, it is important that the refractive index $nF_{b2}$ of the spherical inorganic filler (b2) is in a state of being higher than the refractive index nP of a polymer of the polymerizable monomer (A) and the refractive index $nM_{b1}$ of the organic resin matrix (b1) that constitutes the organic-inorganic composite filler. The refractive index difference between the refractive index $nF_{b2}$ of the spherical inorganic filler (b2) and the refractive index nP of a polymer of the polymerizable monomer (A), and the refractive index difference between the refractive index $nF_{b2}$ of the spherical inorganic filler (b2) and the refractive index $nM_{b1}$ of the organic resin matrix (b1) are preferably 0.001 or more, more preferably 0.002 or more, and even more preferably 0.005 or more.

Furthermore, in a case in which the contrast ratio (Yb/Yw) of a cured product of the curable composition of the present invention is in the range of 0.2 to 0.5 as described above, a colored light induced by interference is clearly exhibited, and the color tone adaptability is enhanced. Therefore, it is preferable that the refractive index difference between the refractive index $nF_{b2}$ of the spherical inorganic filler (b2) and the refractive index nP of a polymer of the polymerizable monomer (A), and the refractive index difference between the refractive index $nF_{b2}$ of the spherical inorganic filler (b2) and the refractive index $nM_{b1}$ of the organic resin matrix (b1) are adjusted to be 0.1 or less, more preferably 0.05 or less, so that transparency is not impaired as far as possible.

The content of the spherical inorganic filler (b2) in the organic-inorganic composite filler is preferably 30% by mass to 95% by mass. When the content of the organic-inorganic composite filler is 30% by mass or more, the colored light of a cured product of the curable composition is satisfactorily exhibited, and the mechanical strength can also be sufficiently increased. Furthermore, it is difficult in view of operation to incorporate the spherical inorganic filler (b2) into the organic-inorganic composite filler at a proportion of more than 95% by mass, and it is difficult to obtain a homogeneous filler. A more suitable content of the spherical inorganic filler (b2) in the organic-inorganic composite filler is 40% by mass to 90% by mass.

Similarly to the spherical particles (B) used as a powder, among the spherical inorganic filler (b2), the refractive index of the silica-titanium group element oxide-based composite oxide, for which the adjustment of the refractive index is easy, is in the range of about 1.45 to 1.58 depending on the content of the silica portion. That is, in the case of using a silica-titanium group element oxide-based composite oxide as the spherical inorganic filler (b2), when the refractive index of the polymerizable monomer (A) is set to the above-mentioned range (in the range of 1.38 to 1.55), the refractive index nP of a polymer obtainable from the polymerizable monomer (A) can be approximately set to the range of 1.40 to 1.57. Therefore, the spherical inorganic filler (b2) can be easily selected so as to satisfy the above-mentioned requirements (formula (3)). That is, a silica-titanium group element oxide-based composite oxide (for example, silica-titania or silica-zirconia) including an adequate amount of silica portion may be used.

In regard to the organic-inorganic composite filler, for the organic resin matrix (b1), a homopolymer or a plurality of copolymers obtainable using the polymerizable monomers such as described as the above-mentioned polymerizable monomer (A) can be selected without any limitations. As described above, in the case of using a silica-titanium group element oxide-based composite oxide, for which the adjustment of the refractive index of the spherical inorganic filler (b2) is easy, since the refractive index thereof is in the range of 1.45 to 1.58 depending on the content of the silica portion, the above-mentioned requirement (formula (2)) can be satisfied by setting the refractive index $nM_{b1}$ of the organic resin matrix (b1) to be approximately in the range of 1.40 to 1.57.

The organic resin matrix (b1) may be identical to or different from the polymer obtainable from the polymerizable monomer (A); however, the refractive index difference between the refractive index $nM_{b1}$ of the organic resin matrix (b1) and the refractive index nP of a polymer of the polymerizable monomer (A) is preferably 0.005 or less, from the viewpoint of transparency of the curable composition thus obtainable. In a case in which the refractive index is larger than 0.005, the curable composition becomes opaque, and the colored light induced by interference becomes weak. Furthermore, from the viewpoint that light diffusibility can be imparted by means of the refractive index difference, and the color tone adaptability between the curable composition and the teeth can be enhanced, the refractive index is more preferably in the range of 0.001 to 0.005.

The method for producing an organic-inorganic composite filler is not particularly limited, and for example, a general production method of mixing predetermined amounts of the respective components of the spherical inorganic filler (b2), the polymerizable monomer, and the polymerization initiator, polymerizing the mixture by a method such as heating or light irradiation, and then pulverizing the polymerization product, can be employed. Alternatively, the production method described in WO 2011/115007 or WO 2013/039169 may also be employed. In this production method, inorganic aggregate particles formed by aggregation of the spherical inorganic filler (b2) are immersed in a polymerizable monomer solvent including a polymerizable monomer, a polymerization initiator, and an organic solvent, subsequently the organic solvent is removed, and the polymerizable monomer is polymerized and cured by a method such as heating or light irradiation. According to the production method described in WO 2011/115007 or WO 2013/039169, an organic-inorganic composite filler in which inorganic primary particles cover the surface of the inorganic primary particles of the aggregated inorganic aggregate particles, an organic resin phase that binds the respective inorganic primary particles is included, and aggregation gaps are formed between the organic resin phase that covers the surface of the respective inorganic primary particles are formed, can be obtained. Regarding the polymerization initiator, any known polymerization initiator can be used without particular limitations; however, in view of obtaining a cured product having lower yellowness, it is preferable to use a thermal polymerization initiator, and it is more preferable to use a thermal polymerization initiator formed from a compound that does not have an aromatic ring in the structure.

The average particle diameter of the organic-inorganic composite filler is not particularly limited; however, from the viewpoint of improving the mechanical strength of the cured product and the operability of the curable paste, the average particle diameter is preferably 2 μm to 100 μm, more preferably 5 μm to 50 μm, and even more preferably 5 μm to 30 μm. Furthermore, the shape is not particularly limited, and examples include an irregularly shaped composite filler obtainable by mixing predetermined amounts of the various components of the spherical inorganic filler (b2), a polymerizable monomer, and a polymerization initiator, polymerizing the mixture by a method such as heating or light irradiation, and then pulverizing the polymerization product; and a spherical or approximately spherical composite filler produced according to the method described in WO 2011/115007 or WO 2013/039169.

The organic-inorganic composite filler may include known additives to the extent that the effects are not impaired. Specific examples of the additives include a pigment, a polymerization inhibitor, and a fluorescent brightening agent. These additives can be used usually at a proportion of 0.0001 parts by mass to 5 parts by mass with respect to 100 parts by mass of the organic-inorganic composite filler.

Furthermore, the organic-inorganic composite filler may be washed or surface-treated using a silane coupling agent or the like.

In a case in which only an organic-inorganic composite filler is used as the spherical particles (B), the incorporation amount of the organic-inorganic composite filler is 50 parts by mass to 1,000 parts by mass with respect to 100 parts by mass of the polymerizable monomer (A), and in order to improve the workability of a paste of the curable composition and the mechanical strength of the cured product, the organic-inorganic composite filler may be incorporated in an amount of 70 parts by mass to 600 parts by mass, and more suitably 100 parts by mass to 400 parts by mass. Furthermore, the incorporation amount of the spherical inorganic filler (b2) in the organic-inorganic composite filler is, as described above, preferably 30% by mass to 95% by mass, and more suitably 40% by mass to 90% by mass. Therefore, the incorporation amount of the spherical inorganic filler that affects exhibition of a colored light induced by interference is from 10% by mass ((50/150)×30%) to 86.4% by mass (1,000/1,100)×95%) in the curable composition. In a case in which spherical particles (B) as a powder and an organic-inorganic composite filler are used in combination, a colored light induced by interference is satisfactorily exhibited by incorporating the inorganic filler component such that the incorporation amount of the inorganic filler component is 10% by mass to 86% by mass in the curable composition. The incorporation amount of the inorganic filler component is more preferably 15% by mass to 86% by mass, and even more preferably 20% by mass to 86% by mass. Furthermore, in order to obtain satisfactory operability of a paste of the curable composition and the mechanical strength of a cured product, it is preferable that the mixing proportions (mass ratio) of the spherical particles (B) and the organic-inorganic composite filler are adjusted to 90:10 to 10:90, more preferably to 80:20 to 20:80, and even more preferably to 70:30 to 30:70.

<Polymerization Initiator (C)>

A polymerization initiator is incorporated for the purpose of polymerizing and curing the present composition, and any known polymerization initiator is used without any particular limitations.

Above all, in a dental direct filling restoration application in which curing is frequently achieved within the oral cavity, a photopolymerization initiator or a chemical polymerization initiator is preferred, and from the viewpoint that a mixing operation is unnecessary, and the operation is convenient, a photopolymerization initiator is more preferred.

Regarding the polymerization initiator used for photopolymerization, benzoin alkyl ethers such as benzoin methyl ether, benzoin ethyl ether, and benzoin isopropyl ether; benzyl ketals such as benzyl dimethyl ketal and benzyl diethyl ketal; benzophenones such as benzophenone, 4,4'-dimethylbenzophenone, and 4-methacryloxybenzophenone; α-diketones such as diacetyl, 2,3-pentadionebenzyl, camphor-quinone, 9,10-phenanthraquinone, and 9,10-anthraquinone; thioxanthone compounds such as 2,4-diethoxythioxanthone, 2-chlorothioxanthone, and methylthioxanthone; and bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis(2,4,6-trimethylbenzoyl)-phenylphosphine oxide, and the like can be used.

Meanwhile, as the photopolymerization initiator, a reducing agent is frequently added, and examples thereof include tertiary amines such as 2-(dimethylamino)ethyl methacrylate, ethyl 4-dimethylaminobenzoate, and N-methyldiethanolamine; aldehydes such as lauryl aldehyde, dimethylaminobenzaldehyde, and terephthalic aldehyde; and sulfur-containing compounds such as 2-mercaptobenzoxazole, 1-decanethiol, thiosalicylic acid, and thiobenzoic acid.

Furthermore, cases of using a composition by adding a photoacid generator, in addition to the photopolymerization initiator and the reducing compound, may be frequently seen. Examples of such a photoacid generator include a diaryliodonium salt-based compound, a sulfonium salt-based compound, a sulfonic acid ester compound, a halomethyl-substituted-S-triazine derivative, and a pyridinium salt-based compound.

These polymerization initiators may be used singly, or two or more kinds thereof may be used as mixtures. Regarding the incorporation amount of the polymerization initiator, an effective amount may be selected according to the purpose; however, the polymerization initiator is usually used at a proportion of 0.01 to 10 parts by mass, and preferably at a proportion of 0.1 to 5 parts by mass, with respect to 100 parts by mass of the polymerizable monomer (A).

<Inorganic Particles (D)>

In the curable composition of the present invention, for the purpose of effectively exhibiting a colored light induced by interference of the cured product and further improving the color tone adaptability, inorganic particles (D) having an average primary-particle diameter of less than 100 nm can be further incorporated in addition to the spherical particles (B) having an average primary-particle diameter in the range of 230 nm to 1,000 nm.

The inorganic particles (D) have an average primary-particle diameter of less than 100 nm, and since this average primary-particle diameter is a particle diameter with which the phenomenon of interference of visible light does not easily occur as described above, exhibition of the colored light induced by interference according to the present invention is not inhibited. Therefore, by incorporating the inorganic particles (D), the contrast ratio of a cured product of the curable composition can be adjusted by the incorporation amount of the inorganic particles (D) while light having a desired color is exhibited.

Regarding the inorganic particles (D), particles that are used as the spherical particles (B) according to the present invention can be used without limitations. Specific examples include inorganic powders such as amorphous silica, silica-titanium group element oxide-based composite oxide particles (silica-zirconia, silica-titania, or the like), quartz, alumina, barium glass, strontium glass, lanthanum glass, fluoroaluminosilicate glass, ytterbium fluoride, zirconia, titania, and colloidal silica.

Among these, from the viewpoint that adjustment of the refractive index is easy, amorphous silica or silica-titanium group element oxide-based composite oxide particles are preferred. The refractive index at 25° C. of amorphous silica or silica-titanium group oxide-based composite oxide particles is, for example, in the range of 1.45 to 1.58.

The silica-titanium group element oxide-based composite oxide particles may be surface-treated with a silane coupling agent, similarly to the spherical particles (B). Through a surface treatment using a silane coupling agent, when the curable composition of the present invention is cured, excellent interfacial strength between the composite oxide particles and the cured product of the polymerizable monomer (A) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be decided after the mechanical properties and the like of a cured product of the curable composition thus obtainable are checked in advance by experiments. An example of a suitable range is the range of 0.1 parts by mass to 15 parts by mass with respect to 100 parts by mass of the inorganic particles (D).

The incorporation amount of the inorganic particles (D) according to the present invention is suitably 0.1 parts by mass to 50 parts by mass, and more suitably 0.2 parts by mass to 30 parts by mass, with respect to 100 parts by mass of the polymerizable monomer (A), from the viewpoint of the color tone adaptability to natural teeth.

<Other Additives>

In the curable composition of the present invention, other known additives can be incorporated in addition to the components (A) to (D) described above, to the extent that the effects are not impaired. Specific examples include a polymerization inhibitor and an ultraviolet absorber.

As described above in the present invention, even if a coloring substance such as a pigment is not used, restoration with satisfactory color tone adaptability to natural teeth is enabled with a single paste (curable composition). Therefore, an embodiment in which a pigment having a risk of being discolored with time is not incorporated is preferred. However, according to the present invention, incorporation of a pigment is not to be denied per se, and a pigment may be incorporated to the extent that does not obstruct the colored light induced by interference of spherical particles. Specifically, a pigment in an amount of about 0.0005 parts by mass to 0.5 parts by mass, and preferably about 0.001 parts by mass to 0.3 parts by mass, with respect to 100 parts by mass of the polymerizable monomer, may be incorporated.

The curable composition of the present invention is particularly suitably used as a dental curable composition as described above, and particularly as a dental filling restorative material represented by a photocurable composite resin; however, the usage is not limited there, and the curable composition can also be suitably used for other dental applications. Examples of the use thereof include dental cement and a restorative material for abutment construction.

EXAMPLES

Hereinafter, the present invention will be more specifically described by way of Examples; however, the present invention is not intended be limited to these Examples.

The methods for measuring various physical properties according to the present invention are as follows.

(1) Average Primary-Particle Diameters of Spherical Particles (B) and Spherical Inorganic Filler (b2)

A photograph of a powder was taken with a scanning electron microscope (manufactured by Philips N.V., "XL-30S") at a magnification ratio of 5,000 to 100,000 times, and the image thus taken was processed using an image analysis software program (manufactured by Asahi Kasei Engineering Corp., "IP-1000PC"). The number (30 or more particles) and the primary-particle diameters (maximum diameters) of particles observed within a unit viewing field of that photograph were measured, and the average primary-particle diameter was calculated by the following formula based on the measured values.

$$\bar{x} = \frac{\sum_{i=1}^{n} x_i}{n} \text{ (Number average)}$$

($n$: number of particles, $x_i$: primary particle diameter (maximum diameter) of $i$-th particle)

(2) Abundance Proportions of Average Particle-Sized Particles of Spherical Particles (B) and Spherical Inorganic Filler (b2)

The proportion (%) of particles present in the range of ±5% based on the average primary-particle diameter of the spherical particles (B) was obtained by measuring, among all particles (30 or more particles) observed within a unit viewing field of the photograph, the number of particles having primary-particle diameters (maximum diameters) outside the particle diameter range of ±5% based on the average primary-particle diameter determined as described above, subtracting the value from the number of all particles, thereby determining the number of particles in the particle diameter range of ±5% based on the average primary-particle diameter within the unit viewing field of the photograph, and calculating the proportion by the following formula.

Proportion(%)of particles in range of ±5% based on average primary-particle diameter of spherical filler ($B$)=[(Number of particles in particle diameter range of ±5% based on average primary-particle diameter within unit viewing field of scanning electron microscopic photograph)/ (total number of particles within unit viewing field of scanning electron microscopic photograph)]×100

(3) Average Uniformity of Spherical Particles (B) and Spherical Inorganic Filler (b2)

A photograph of a powder was taken with a scanning electron microscope, and for the particles observed within a unit viewing field of the photograph, the number (n: 30 or more), the maximum diameter of each particle as the major axis (Li), and the diameter in a direction orthogonally intersecting the major axis as the minor axis (Bi) were determined. Thus, the average uniformity was calculated by the following formula.

$$\text{Average uniformity} = \frac{\sum_{i=1}^{n} Bi/Li}{n}$$

(4) Average Particle Diameter (Particle Size) of Organic-Inorganic Composite Filler 0.1 g of an organic-inorganic composite filler was dispersed in 10 mL of ethanol, and the dispersion was irradiated with ultrasonic waves for 20 minutes. The median diameter of volume statistics was determined by applying an optical model "Fraunhofer" using a particle size distribution meter (manufactured by Beckman Coulter, Inc., "LS230") according to a laser diffraction-scattering method.

(5) Measurement of Refractive Index

<Refractive Index of Polymerizable Monomer (A)>

The refractive index of the polymerizable monomer (or a mixture of polymerizable monomers) used was measured in a constant temperature chamber at 25° C. using an Abbe refractometer (manufactured by Atago Co., Ltd.).

<Refractive Index (nP) of Polymer of Polymerizable Monomer (A)>

The refractive index of a polymer of the polymerizable monomer (or a mixture of polymerizable monomers) used was measured using a polymer polymerized under conditions almost the same as the polymerization conditions in a cavity, in a constant temperature chamber at 25° C. using an Abbe refractometer (manufactured by Atago Co., Ltd.).

That is, a uniform polymerizable monomer (or a mixture of polymerizable monomers) obtained by mixing 0.2% by mass of camphor-quinone, 0.3% by mass of ethyl N,N-dimethyl-p-benzoate, and 0.15% by mass of hydroquinone monomethyl ether was introduced into a mold having a hole having a size of 7 mmϕ×0.5 mm, and a polyester film was pressure-welded on both surfaces. Subsequently, the polymerizable monomer was cured by irradiating the monomer with light for 30 seconds using a halogen type dental light irradiator (manufactured by Sybron Dental Specialties, Inc., "Demetron LC") at a quantity of light of 500 mW/cm$^2$, and then the cured product was removed from the mold. Thus, a polymer of the polymerizable monomer was produced. When the polymer was placed in an Abbe refractometer (manufactured by Atago Co., Ltd.), for the purpose of tightly adhering the polymer with the measuring surface, a solvent which does not dissolve the sample and having a refractive index higher than that of the sample (bromonaphthalene) was added dropwise to the sample, and the refractive index was measured.

<Refractive Index $nM_{b1}$ of Organic Resin Matrix (b1)>

The refractive index of the organic resin matrix was measured in a constant temperature chamber at 25° C. using a polymer obtained by polymerizing under almost the same conditions as the polymerization conditions at the time of producing the organic-inorganic composite filler, using an Abbe refractometer (manufactured by Atago Co., Ltd.).

That is, a uniform polymerizable monomer (or a mixture of polymerizable monomers) mixed with 0.5% by mass of azobisisobutyronitrile was introduced into a mold having a hole having a size of 7 mmφ×0.5 mm, and a polyester film was pressure-welded on both surfaces. Then, the polymerizable monomer was heated for one hour under an added pressure of nitrogen and was polymerized and cured. Subsequently, the resultant was removed from the mold, and thus a polymer of the polymerizable monomer (organic resin matrix) was produced. When the polymer was placed in an Abbe refractometer (manufactured by Atago Co., Ltd.), for the purpose of tightly adhering the polymer with the measuring surface, a solvent which does not dissolve the sample and having a higher refractive index than the sample (bromonaphthalene) was added dropwise to the sample, and the refractive index was measured.

<Refractive Indices of Spherical Particles (B), Spherical Inorganic Filler (b2), and Inorganic Particles (D)>

The refractive indices of the spherical particles, the spherical inorganic filler, and the inorganic particles used were measured according to a liquid immersion method using an Abbe refractometer (manufactured by Atago Co., Ltd.).

That is, in a constant temperature chamber at 25° C., 1 g of a spherical inorganic filler or inorganic particles, or a surface-treated product thereof was dispersed in 50 mL of anhydrous toluene in a 100-mL sample bottle. While this dispersion liquid was stirred with a stirrer, 1-bromotoluene was added dropwise in small amounts, the refractive index of the dispersion liquid at the time point when the dispersion liquid became most transparent was measured, and the value thus obtained was designated as the refractive index of the inorganic filler material.

(6) Evaluation of Colored Light by Visual Inspection

A paste of each of the curable compositions produced in Examples and Comparative Examples was introduced into a mold having a hole having a size of 7 mmφ×1 mm, and a polyester film was pressure-welded on both surfaces. Both surfaces were cured by irradiating with light for 30 seconds with a visible light irradiator (manufactured by Tokuyama Corp., POWER LIGHT), and then the resultant was removed from the mold. The cured product was mounted on an adhesive surface of a black tape (carbon tape) that measured about 10 mm on each edge, and the color tone of colored light was checked by visual inspection.

(7) Wavelength of Colored Light

A paste of each of the curable compositions produced in Examples and Comparative Examples was introduced into a mold having a hole having a size of 7 mmφ×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The spectral reflectance was measured using a color difference meter (manufactured by Tokyo Denshoku Co., Ltd., "TC-1800 MKII") on the black background color and on the white background color, and the maximum point of the reflectance on the black background color was designated as the wavelength of the colored light.

(8) Evaluation of Contrast Ratio (Yb/Yw) of Curable Composition

A paste of each of the curable compositions produced in Examples and Comparative Examples was introduced into a mold having a hole having a size of 7 mmφ×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The Y values (black background color and white background color) of the tristimulus values of the cured product were measured using a color difference meter (manufactured by Tokyo Denshoku Co., Ltd., "TC-1800 MKII"). The contrast ratio (Yb/Yw) was calculated on the basis of the following formula.

Contrast ratio($Yb/Yw$)=$Y$ value in case of black background color/$Y$ value in case of white background color (9) Evaluation of Color Tone Adaptability Using Colorimeter A hard resin tooth that reproduced a Class I cavity (diameter 4 mm, depth 1 mm) at the central portion of the occlusal surface of lower right No. 6 and a hard resin tooth that reproduced a Class I cavity (diameter 4 mm, depth 5 mm) at the central portion of the occlusal surface of lower right No. 6 were used. The defective part was filled with a curable composition, the curable composition was cured and polished, and the color tone adaptability was evaluated with a two-dimensional colorimeter (manufactured by Papalab Co., Ltd., "RC-500"). Meanwhile, as the hard resin teeth, a hard resin tooth of high chroma (corresponding to A4) and a hard resin tooth of low chroma (corresponding to A1) in the class of A system (red-brown) according to Shade Guide "VITA Classical", and a hard resin tooth of high chroma (corresponding to B4) and a hard resin tooth of low chroma (corresponding to B1) in the class of B system (red-yellow) according to Shade Guide "VITA Classical" were used.

A hard resin tooth was mounted on the two-dimensional colorimeter, an image of the hard resin tooth was captured, and then processing of the captured image was performed using an image analysis software program (manufactured by Papalab Co., Ltd., "RC Series Image Viewer"). The color difference (ΔE* according to CIELab) between the colorimetric values of a restored portion and a non-restored portion of the hard resin tooth was determined, and thus evaluation of the color tone adaptability was performed.

$$\Delta_E{}^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

Meanwhile, L1*: lightness index of restored portion of hard resin tooth, a1* and b1*: chroma indices of restored portion of hard resin tooth, L2*: lightness index of restored portion of hard resin tooth, a2* and b2*: chroma indices of restored portion of hard resin tooth, ΔE*: amount of change in color tone.

(10) Evaluation of Color Tone Adaptability by Visual Inspection

A hard resin tooth that reproduced a Class I cavity (diameter 4 mm, depth 1 mm) at the central portion of the occlusal surface of lower right No. 6 and a hard resin tooth that reproduced a Class I cavity (diameter 4 mm, depth 5 mm) at the occlusal surface of lower right No. 6 were used. The defective part was filled with a curable composition, the curable composition was cured and polished, and the color tone adaptability was checked by visual inspection. Meanwhile, as the hard resin teeth, a hard resin tooth of high chroma (corresponding to A4) and a hard resin tooth of low chroma (corresponding to A1) in the class of A system (red-brown) according to Shade Guide "VITA Classical", and a hard resin tooth of high chroma (corresponding to B4) and a hard resin tooth of low chroma (corresponding to B1) in the class of B system (red-yellow) according to Shade Guide "VITA Classical" were used.

—Evaluation Criteria—

5: The color tone of the restoration product is indistinguishable from that of the hard resin tooth.
4: The color tone of the restoration product highly matches with that of the hard resin tooth.
3: The color tone of the restoration product is similar to that of the hard resin tooth.
2: The color tone of the restoration product is similar to that of the hard resin tooth; however, adaptability is not satisfactory.
1: The color tone of the restoration product does not match with that of the hard resin tooth.

The polymerizable monomers, polymerization initiators, inorganic particles, and the like used in Examples and Comparative Examples were as follows.

[Polymerizable Monomers]
  1,6-Bis(methacrylethyloxycarbonylamino)trimethylhexane (hereinafter, abbreviated to "UDMA")
  Triethylene glycol dimethacrylate (hereinafter, abbreviated to "3G")
  2,2-Bis[(3-methacryloyloxy-2-hydroxypropyloxy)phenyl]propane (hereinafter, abbreviated to "bis-GMA")

[Polymerization Initiator]
  Camphor-quinone (hereinafter, abbreviated to "CQ")
  Ethyl N,N-dimethyl-p-benzoate (hereinafter, abbreviated to "DMBE")
  Azobisisobutyronitrile (hereinafter, abbreviated to "AIBN") [Polymerization inhibitor]
  Hydroquinone monomethyl ether (hereinafter, abbreviated to "HQME")

[Inorganic Particles]
  RHEOROSIL QS-102 (primary particle diameter 5 nm to 50 nm, manufactured by Tokuyama Corp.)

[Colorant]
  Titanium dioxide (white pigment)
  Pigment Yellow (yellow pigment)
  Pigment Red (red pigment)
  Pigment Blue (blue pigment)

[Preparation of Mixture of Polymerizable Monomers]

The polymerizable monomers shown in Table 1 were mixed, and polymerizable monomers M1, M2, M3, and M4 were produced. The values in the parentheses in Table 1 represent the use amounts (unit: parts by mass) of the respective polymerizable monomers.

TABLE 1

| | Polymerizable monomer | Refractive index | |
| | | Before curing | After curing |
|---|---|---|---|
| M1 | UDMA(60)/3G(40) | 1.474 | 1.509 |
| M2 | bis-GMA(50)/3G(50) | 1.506 | 1.540 |
| M3 | bis-GMA(1)/3G(40)/UDMA(59) | 1.474 | 1.510 |
| M4 | bis-GMA(8)/3G(40)/UDMA(52) | 1.479 | 1.514 |

[Production of Spherical Particles, Spherical Inorganic Filler, and Irregularly Shaped Inorganic Filler]

Spherical particles and a spherical inorganic filler were produced by the methods described in Japanese Unexamined Patent Application, Publication No. S58-110414, Japanese Unexamined Patent Application, Publication No. S58-156524, and the like. That is, spherical particles and a spherical inorganic filler were produced using a so-called sol-gel method of adding a mixed solution including a hydrolyzable organosilicon compound (tetraethyl silicate or the like) and a hydrolyzable organic titanium group metal compound (tetrabutyl zirconate, tetrabutyl titanate, or the like) into an ammoniacal alcohol (for example, methanol, ethanol, isopropyl alcohol, or isobutyl alcohol) solution having aqueous ammonia incorporated therein, performing hydrolysis, and precipitating out a reaction product. Subsequently, the particles were prepared using a method of drying the resultant, pulverizing the dried product as necessary, and calcining the pulverization product.

An irregularly shaped inorganic filler was produced by the method described in Japanese Unexamined Patent Application, Publication No. H02-132102, Japanese Unexamined Patent Application, Publication No. H03-197311, or the like. That is, an irregularly shaped inorganic filler was produced using a method of dissolving an alkoxysilane compound in an organic solvent, adding water to this solution to perform partial hydrolysis, further adding thereto an alkoxide of another metal and an alkali metal compound to be compounded, thereby performing hydrolysis to produce a gel-like material, subsequently drying the gel-like material, subsequently pulverizing the dried product as necessary, and calcining the pulverization product.

The spherical particles, spherical inorganic filler, and irregularly shaped inorganic filler used in Examples are shown in Table 2.

TABLE 2

| | Composition and shape of filler | | Average particle diameter (nm) | Refractive index | Abundance proportion of average particle-sized particles[1] (%) | Average uniformity |
| | Composition (mol %) | Shape | | | | |
|---|---|---|---|---|---|---|
| PF1 | $SiO_2/ZrO_2/Na_2O$ = 89.8/9.0/1.2 | Spherical | 178 | 1.515 | 91 | 0.98 |
| PF2 | $SiO_2/ZrO_2/Na_2O$ = 89.8/9.0/1.2 | Spherical | 230 | 1.515 | 92 | 0.97 |
| PF3 | $SiO_2/ZrO_2/Na_2O$ = 89.8/9.0/1.2 | Spherical | 303 | 1.515 | 90 | 0.92 |
| PF4 | $SiO_2/ZrO_2/Na_2O$ = 89.8/9.0/1.2 | Spherical | 80 | 1.515 | 92 | 0.94 |
| PF5 | $SiO_2/ZrO_2/Na_2O$ = 89.8/9.0/1.2 | Spherical | 280 | 1.515 | 94 | 0.94 |
| PF6 | $SiO_2/ZrO_2/Na_2O$ = 88.7/10.1/1.2 | Spherical | 282 | 1.522 | 93 | 0.92 |

TABLE 2-continued

| | Composition and shape of filler | | Average particle diameter (nm) | Refractive index | Abundance proportion of average particle-sized particles[1] (%) | Average uniformity |
|---|---|---|---|---|---|---|
| | Composition (mol %) | Shape | | | | |
| PF7 | $SiO_2/ZrO_2/Na_2O$ = 83.9/14.3/1.8 | Spherical | 286 | 1.542 | 91 | 0.90 |
| PF8 | $SiO_2/TiO_2/Na_2O$ = 90.1/8.7/1.2 | Spherical | 280 | 1.522 | 95 | 0.95 |
| PF9 | $SiO_2/TiO_2/Na_2O$ = 90.6/7.6/1.8 | Spherical | 281 | 1.515 | 93 | 0.96 |
| PF10 | $SiO_2/ZrO_2/Ma_2O$ = 88.7/10.1/1.2 | Spherical | 340 | 1.522 | 88 | 0.93 |
| PF11 | $SiO_2/ZrO_2/Na_2O$ = 88.7/10.1/1.2 | Spherical | 260 | 1.522 | 93 | 0.94 |
| PF12 | $SiO_2/ZrO_2/Na_2O$ = 89.8/9.0/1.2 | Irregularly shaped | 500 | 1.515 | 50 | — |

[1]The abundance proportion of the average particle-sized particles is the proportion (%) of particles present in ±5% based on the average particle diameter.

[Production of Irregularly Shaped Organic-Inorganic Composite Filler]

0.5% by mass of a thermal polymerization initiator (AIBN) was dissolved in advance in the polymerizable monomers shown in Table 1, a predetermined amount (Table 3) of the spherical inorganic filler or irregularly shaped inorganic filler shown in Table 2 was added and mixed with the solution, and the resultant was made into a paste with a mortar. This paste was heated for one hour under an added pressure of nitrogen at 95° C., and thereby the paste was polymerized and cured. This cured product was pulverized using a vibratory ball mill, and was surface-treated by heating to reflux for 5 hours at 90° C. in ethanol using 0.02% by mass of γ-methacryloyloxypropyltrimethoxysilane. Thus, irregularly shaped organic-inorganic composite fillers CF1 to CF12 as shown in the following Table 3 were obtained. The values in the parentheses in Table 3 represent the amounts of use (unit: parts by mass) of the polymerizable monomers and spherical inorganic fillers.

[Production of Approximately Spherical Organic-Inorganic Composite Filler]

200 g of water was added to 100 g of a spherical inorganic filler shown in Table 2, and an aqueous dispersion of these was obtained using a circulation type pulverizer SC MILL (manufactured by Nippon Coke & Engineering Co., Ltd.).

On the other hand, 4 g (0.016 mol) of γ-methacryloyloxypropyltrimethoxysilane and 0.003 g of acetic acid were added to 80 g of water, and the mixture was stirred for 1 hour and 30 minutes. Thus, a uniform solution at pH 4 was obtained. This solution was added to the spherical inorganic filler dispersion liquid, and the mixture was mixed until the dispersion liquid became uniform. Subsequently, while the dispersion liquid was lightly mixed, the dispersion liquid was supplied onto a disc rotating at high speed and was granulated by a spray drying method.

Spray drying was carried out using a spray dryer TSR-2W (manufactured by Sakamoto Giken Co., Ltd.) that includes a rotating disc and sprays by means of centrifugal force. The speed of rotation of the disc was 10,000 rpm, and the temperature of air in a dry atmosphere was 200° C. Subsequently, a powder obtained by being granulated by spraying and drying was dried in a vacuum at 60° C. for 18 hours, and 73 g of approximately spherically shaped aggregates were obtained.

Next, a predetermined amount (Table 3) of the aggregates were added to and immersed in a polymerizable monomer solution (including 36 parts by mass of a polymerizable monomer with respect to 100 parts by mass of an organic solvent) obtained by adding 0.5% by mass of AIBN as a thermal polymerization initiator into the polymerizable monomer shown in Table 1, and mixing the mixture with methanol as an organic solvent. The mixture was sufficiently stirred, it was checked that this mixture was brought to a slurry state, and then the slurry was left to stand for one hour.

The above-described mixture was transferred into a rotary evaporator. In a stirred state, the mixture was dried for one hour under the conditions of a degree of pressure reduction of 10 hPa and a heating condition of 40° C. (a warm water bath was used), and the organic solvent was removed. When the organic solvent was removed, a powder having high fluidity was obtained.

While the powder thus obtained was stirred in a rotary evaporator, the powder was heated for one hour under the conditions of a degree of pressure reduction of 10 hPa and a heating condition of 100° C. (an oil bath was used), and thereby the polymerizable monomer in the powder was polymerized and cured. Through this operation, 9 g each of approximately spherical organic-inorganic composite fillers CF13 to CF20 shown in the following Table 3, in which the surface of aggregates of the spherical inorganic filler was coated with an organic polymer, was obtained.

TABLE 3

| | Composition and shape of organic-inorganic composite filler | | | Filler packing ratio (wt %) | Average particle diameter (μm) |
|---|---|---|---|---|---|
| | Matrix (b1) | Inorganic filler (b2) | Shape | | |
| CF1 | M1(100) | PF1(300) | Irregularly shaped | 75 | 30 |
| CF2 | M1(100) | PF2(300) | Irregularly shaped | 75 | 28 |
| CF3 | M1(100) | PF3(300) | Irregularly shaped | 75 | 31 |
| CF4 | M1(100) | PF4(300) | Irregularly shaped | 75 | 24 |
| CF5 | M1(100) | PF5(300) | Irregularly shaped | 75 | 29 |
| CF6 | M1(100) | PF6(300) | Irregularly shaped | 75 | 26 |
| CF7 | M2(100) | PF7(300) | Irregularly shaped | 75 | 25 |
| CF8 | M1(100) | PF8(300) | Irregularly shaped | 75 | 24 |
| CF9 | M1(100) | PF12(300) | Irregularly shaped | 75 | 28 |

TABLE 3-continued

| | Composition and shape of organic-inorganic composite filler | | | Filler packing ratio (wt %) | Average particle diameter (μm) |
|---|---|---|---|---|---|
| | Matrix (b1) | Inorganic filler (b2) | Shape | | |
| CF10 | M1(100) | PF5(233) | Irregularly shaped | 70 | 28 |
| CF11 | M1(100) | PF5(150) | Irregularly shaped | 60 | 33 |
| CF12 | M1(100) | PF5(400) | Irregularly shaped | 80 | 31 |
| CF13 | M1(100) | PF1(300) | Approximately spherical | 75 | 32 |
| CF14 | M1(100) | PF2(300) | Approximately spherical | 75 | 31 |
| CF15 | M1(100) | PF3(300) | Approximately spherical | 75 | 33 |
| CF16 | M1(100) | PF4(300) | Approximately spherical | 75 | 29 |
| CF17 | M1(100) | PF10(300) | Approximately spherical | 75 | 30 |
| CF18 | M1(100) | PF5(300) | Approximately spherical | 75 | 33 |
| CF19 | M2(100) | PF5(300) | Approximately spherical | 75 | 34 |
| CF20 | M4(100) | PF5(300) | Approximately spherical | 75 | 32 |

Examples 1 to 29

0.3% by mass of CQ, 1.0% by weight of DMBE, and 0.15% by mass of HQME were added to the polymerizable monomers M1, M2, M3, or M4, and the components were mixed. Thus, uniform polymerizable monomer compositions were prepared. Next, each of the fillers shown in Table 2 and Table 3 was weighed in a mortar, each of the above-mentioned polymerizable monomers was slowly added thereto under red light, and the mixture was sufficiently kneaded in the dark to obtain a uniform curable paste. This paste was further degassed under reduced pressure to eliminate air bubbles, and thus a curable composition was produced. For the curable composition thus obtained, various physical properties were evaluated based on the above-described methods. The compositions and results are shown in Table 4 to Table 6. The values in the parentheses in Table 4 represent the amounts of use (unit: parts by mass) of the various components.

Comparative Examples 1 to 8, 10 to 12

0.3% by mass of CQ, 1.0% by mass of DMBE, and 0.15% by mass of HQME were added to the polymerizable monomer M1, M2, or M4, the components were mixed, and thus uniform polymerizable monomer compositions were produced. Next, each of the various fillers shown in Table 2 and Table 3 was weighed in a mortar, each of the above-mentioned polymerizable monomers was slowly added thereto under red light, and the mixture was sufficiently kneaded in the dark to obtain a uniform curable paste. This paste was further degassed under reduced pressure to eliminate air bubbles, and thus a curable composition was produced. For the curable composition thus obtained, various physical properties were evaluated based on the above-described methods. The compositions and results are shown in Table 4 to Table 6.

Comparative Example 9

0.3% by mass of CQ, 1.0% by mass of DMBE, and 0.15% by mass of HQME were added to the polymerizable monomer M1, and the components were mixed. Thus, a uniform polymerizable monomer composition was produced. Next, the organic-inorganic composite filler shown in Table 3 was weighed in a mortar, and the above-mentioned polymerizable monomer was slowly added thereto under red light. Furthermore, 0.040 g of titanium dioxide (white pigment), 0.0008 g of Pigment Yellow (yellow pigment), 0.0004 g of Pigment Red (red pigment), and 0.0002 g of Pigment Blue (blue pigment) were added to the mixture, and the mixture was sufficiently kneaded in the dark to obtain a uniform curable paste. Furthermore, this paste was degassed under reduced pressure to eliminate air bubbles, and pigments were added in the composition shown in Comparative Example 2. Thus, a curable composition adjusted to a color tone (corresponding to A4) that matched with A system of high-chroma hard resin teeth was produced. Through an evaluation by visual inspection, a color tone (corresponding to A4) that matched with A system of high-chroma hard resin teeth was obtained. Subsequently, various physical properties were evaluated based on the above-described methods. The composition and results are shown in Table 4 to Table 6.

TABLE 4

| | Polymerizable monomer (A) | Organic-inorganic composite filler | Spherical particles (B) | Inorganic particles (B) | Refractive index difference [1] | Evaluation of colored light by visual inspection | Wavelength (nm) of colored light on black background | Wavelength (nm) of colored light on white background | Cured product contrast ratio (Yb/Yw) |
|---|---|---|---|---|---|---|---|---|---|
| Example 1 | M1 (100) | CF2 (400) | — | — | 0 | Yellow | 607 | No maximum | 0.42 |
| Example 2 | M1 (100) | CF3 (400) | — | — | 0 | Red | 756 | No maximum | 0.43 |
| Example 3 | M1 (100) | CF5 (400) | — | — | 0 | Red | 748 | No maximum | 0.40 |
| Example 4 | M1 (100) | CF5 (240) | PF5 (160) | — | 0 | Red | 757 | No maximum | 0.39 |
| Example 5 | M1 (100) | — | PF5 (300) | — | — | Red | 740 | No maximum | 0.29 |
| Example 6 | M1 (100) | CF5 (240) | PF5 (160) | 0.5 | 0 | Red | 755 | No maximum | 0.39 |
| Example 7 | M2 (100) | CF7 (400) | — | — | 0 | Red | 748 | No maximum | 0.41 |
| Example 8 | M3 (100) | CF5 (400) | — | — | −0.001 | Red | 746 | No maximum | 0.41 |
| Example 9 | M4 (100) | CF5 (400) | — | — | −0.005 | Red | 757 | No maximum | 0.42 |
| Example 10 | M1 (100) | CF6 (400) | — | — | 0 | Red | 7S6 | No maximum | 0.43 |
| Example 11 | M1 (100) | CF8 (400) | — | — | 0 | Red | 751 | No maximum | 0.45 |
| Example 12 | M1 (100) | CF10 (240) | — | — | 0 | Red | 754 | No maximum | 0.38 |
| Example 13 | M1 (100) | CF11 (240) | PF5 (160) | — | 0 | Red | 756 | No maximum | 0.35 |
| Example 14 | M1 (100) | CF12 (240) | PF5 (160) | — | 0 | Red | 757 | No maximum | 0.40 |
| Example 15 | M1 (100) | CF6 (300) | PF5 (160) | — | 0 | Red | 740 | No maximum | 0.46 |
| Example 16 | M1 (100) | CF5 (300) | PF9 (100) | — | 0 | Red | 754 | No maximum | 0.41 |

TABLE 4-continued

|  | Polymerizable monomer (A) | Organic-inorganic composite filler | Spherical particles (B) | Inorganic particles (B) | Refractive index difference [1] | Evaluation of colored light by visual inspection | Wavelength (nm) of colored light on black background | Wavelength (nm) of colored light on white background | Cured product contrast ratio (Yb/Yw) |
|---|---|---|---|---|---|---|---|---|---|
| Example 17 | M1 (100) | CF5 (100) | PF5 (300) | — | 0 | Red | 752 | No maximum | 0.37 |
| Example 18 | M1 (100) | CF5 (240) | PF5 (158) | 2 | −0.005 | Red | 753 | No maximum | 0.44 |
| Example 19 | M1 (100) | CF14 (400) | — | — | 0 | Yellow | 610 | No maximum | 0.38 |
| Example 20 | M1 (100) | CF15 (400) | — | — | 0 | Red | 752 | No maximum | 0.38 |
| Example 21 | M1 (100) | CF18 (400) | — | — | 0 | Red | 756 | No maximum | 0.36 |
| Example 22 | M1 (100) | CF20 (400) | — | — | 0 | Red | 754 | No maximum | 0.39 |
| Example 23 | M1 (100) | CF18 (300) | PF5 (100) | — | 0 | Red | 754 | No maximum | 0.36 |
| Example 24 | M1 (100) | CF18 (200) | PF5 (200) | — | 0 | Red | 753 | No maximum | 0.35 |
| Example 25 | M1 (100) | CF18 (100) | PF5 (300) | — | 0 | Red | 751 | No maximum | 0.34 |
| Example 26 | M1 (100) | CF18 (240) | PF5 (155) | 0.5 | 0 | Red | 754 | No maximum | 0.35 |
| Example 27 | M1 (100) | CF18 (240) | PF5 (155) | 5 | 0 | Red | 752 | No maximum | 0.38 |
| Example 28 | M1 (100) | CF18 (240) | PF5 (150) | 10 | 0 | Red | 749 | No maximum | 0.42 |
| Example 29 | M1 (100) | CF18 (395) | — | 5 | 0 | Red | 755 | No maximum | 0.39 |
| Comparative Example 1 | M1 (100) | CF1 (400) | — | — | 0 | Blue | 480 | No Maximum | 0.19 |
| Comparative Example 2 | M1 (100) | CF4 (400) | — | — | 0 | None | 403 | No Maximum | 0.15 |
| Comparative Example 3 | M1 (100) | CF9 (400) | — | — | 0 | None | No maximum | No Maximum | 0.39 |
| Comparative Example 4 | M1 (100) | CF13 (400) | — | — | 0 | Blue | 479 | No Maximum | 0.13 |
| Comparative Example 5 | M1 (100) | CF17 (400) | — | — | 0 | None | 405 | No Maximum | 0.12 |
| Comparative Example 6 | M1 (100) | CF17 (400) | — | — | 0 | Pale red | 741 | No Maximum | 0.35 |
| Comparative Example 7 | M1 (100) | CF19 (400) | — | — | 0 | Blue | 477 | No Maximum | 0.43 |
| Comparative Example 8 | M1 (100) | — | PF1 (300) | — | — | Blue | 474 | No Maximum | 0.17 |
| Comparative Example 9 | M1 (100) | CF4 (400) | — | — | 0 | Red | No Maximum | No Maximum | 0.35 |
| Comparative Example 10 | M1 (100) | — | PF12 (300) | — | — | None | No Maximum | No Maximum | 0.34 |
| Comparative Example 11 | M1 (100) | CF5 (200) | PF5 (100) | 100 | 0 | Pale red | 738 | No Maximum | 0.59 |
| Comparative Example 12 | M1 (100) | — | PF5 (100) | — | — | None | 739 | No Maximum | 0.07 |

[1] Refractive index of polymer of polymerizable monomer (A) − Refractive index of organic resin matrix (b1)

TABLE 5

| | A system (red-brown) color tone adaptability | | | | | | | |
|---|---|---|---|---|---|---|---|---|
| | Low chroma | | | | High chroma | | | |
| | 1 mm | | 5 mm | | 1 mm | | 5 mm | |
| | Evaluation by visual inspection | ΔE* | Evaluation by visual inspection | ΔE* | Evaluation by visual inspection | ΔE* | Evaluation by visual inspection | ΔE* |
| Example 1 | 4 | 0.82 | 4 | 0.97 | 4 | 0.85 | 3 | 2.05 |
| Example 2 | 4 | 0.86 | 4 | 1.21 | 4 | 0.91 | 4 | 1.35 |
| Example 3 | 5 | 0.20 | 5 | 0.45 | 5 | 0.18 | 4 | 0.79 |
| Example 4 | 5 | 0.13 | 5 | 0.27 | 5 | 0.11 | 5 | 0.33 |
| Example 5 | 5 | 0.32 | 4 | 1.01 | 5 | 0.29 | 4 | 1.11 |
| Example 6 | 5 | 0.12 | 5 | 0.24 | 5 | 0.16 | 5 | 0.27 |
| Example 7 | 4 | 1.28 | 4 | 1.34 | 4 | 1.19 | 3 | 1.88 |
| Example 8 | 5 | 0.20 | 5 | 0.33 | 5 | 0.22 | 5 | 0.31 |
| Example 9 | 5 | 0.15 | 5 | 0.21 | 5 | 0.14 | 4 | 0.84 |
| Example 10 | 5 | 0.23 | 5 | 0.30 | 5 | 0.22 | 5 | 0.39 |
| Example 11 | 5 | 0.35 | 5 | 0.42 | 5 | 0.36 | 5 | 0.47 |
| Example 12 | 5 | 0.22 | 5 | 0.34 | 5 | 0.24 | 5 | 0.38 |
| Example 13 | 5 | 0.31 | 4 | 1.09 | 5 | 0.34 | 4 | 1.16 |
| Example 14 | 5 | 0.26 | 5 | 0.35 | 5 | 0.27 | 5 | 0.34 |
| Example 15 | 5 | 0.33 | 5 | 0.56 | 5 | 0.62 | 4 | 1.21 |
| Example 16 | 5 | 0.17 | 5 | 0.29 | 5 | 0.21 | 5 | 0.40 |
| Example 17 | 5 | 0.12 | 5 | 0.21 | 5 | 0.14 | 5 | 0.25 |
| Example 18 | 5 | 0.16 | 5 | 0.22 | 5 | 0.15 | 5 | 0.19 |
| Example 19 | 4 | 1.45 | 4 | 1.67 | 4 | 1.55 | 3 | 2.76 |
| Example 20 | 4 | 1.48 | 5 | 1.62 | 4 | 1.51 | 4 | 1.59 |

TABLE 5-continued

| | A system (red-brown) color tone adaptability | | | | | | | |
|---|---|---|---|---|---|---|---|---|
| | Low chroma | | | | High chroma | | | |
| | 1 mm | | 5 mm | | 1 mm | | 5 mm | |
| | Evaluation by visual inspection | ΔE* | Evaluation by visual inspection | ΔE* | Evaluation by visual inspection | ΔE* | Evaluation by visual inspection | ΔE* |
| Example 21 | 5 | 0.23 | 5 | 0.36 | 5 | 0.22 | 5 | 0.29 |
| Example 22 | 5 | 0.26 | 5 | 0.31 | 5 | 0.22 | 5 | 0.37 |
| Example 23 | 5 | 0.25 | 5 | 0.41 | 5 | 0.28 | 5 | 0.46 |
| Example 24 | 5 | 0.26 | 5 | 0.48 | 5 | 0.27 | 5 | 0.47 |
| Example 25 | 5 | 0.31 | 5 | 0.52 | 5 | 0.33 | 4 | 1.07 |
| Example 26 | 5 | 0.24 | 5 | 0.31 | 5 | 0.28 | 5 | 0.41 |
| Example 27 | 5 | 0.15 | 5 | 0.20 | 5 | 0.14 | 5 | 0.17 |
| Example 28 | 5 | 0.16 | 5 | 0.23 | 5 | 0.14 | 5 | 0.18 |
| Example 29 | 5 | 0.16 | 5 | 0.24 | 5 | 0.13 | 5 | 0.20 |
| Comparative Example 1 | 2 | 3.67 | 1 | 4.61 | 2 | 3.89 | 1 | 4.66 |
| Comparative Example 2 | 2 | 3.72 | 1 | 4.55 | 2 | 3.77 | 1 | 4.52 |
| Comparative Example 3 | 2 | 4.01 | 1 | 4.98 | 2 | 3.65 | 1 | 4.49 |
| Comparative Example 4 | 1 | 4.58 | 1 | 5.01 | 2 | 3.71 | 1 | 4.36 |
| Comparative Example 5 | 1 | 4.87 | 1 | 5.46 | 1 | 4.91 | 1 | 5.67 |
| Comparative Example 6 | 3 | 3.22 | 2 | 4.15 | 3 | 3.19 | 2 | 3.88 |
| Comparative Example 7 | 2 | 3.77 | 2 | 4.00 | 1 | 4.67 | 1 | 6.01 |
| Comparative Example 8 | 1 | 4.66 | 1 | 4.21 | 1 | 3.87 | 1 | 4.42 |
| Comparative Example 9 | 1 | 7.89 | 1 | 7.56 | 4 | 1.55 | 4 | 1.65 |
| Comparative Example 10 | 2 | 3.99 | 1 | 4.57 | 1 | 4.71 | 1 | 5.34 |
| Comparative Example 11 | 2 | 4.11 | 3 | 3.11 | 2 | 4.08 | 2 | 4.21 |
| Comparative Example 12 | 3 | 3.35 | 1 | 4.72 | 2 | 3.96 | 1 | 5.88 |

TABLE 6

| | B system (red-yellow) color tone adaptability | | | | | | | |
|---|---|---|---|---|---|---|---|---|
| | Low chroma | | | | High chroma | | | |
| | 1 mm | | 5 mm | | 1 mm | | 5 mm | |
| | Evaluation by visual inspection | ΔE* | Evaluation by visual inspection | ΔE* | Evaluation by visual inspection | ΔE* | Evaluation by visual inspection | ΔE* |
| Example 1 | 4 | 0.96 | 4 | 1.18 | 4 | 0.99 | 4 | 1.31 |
| Example 2 | 4 | 0.78 | 4 | 1.09 | 4 | 0.95 | 4 | 1.17 |
| Example 3 | 5 | 0.33 | 5 | 0.46 | 4 | 1.24 | 4 | 1.47 |
| Example 4 | 5 | 0.27 | 5 | 0.44 | 5 | 0.25 | 5 | 0.37 |
| Example 5 | 5 | 0.31 | 4 | 0.91 | 5 | 0.29 | 3 | 2.66 |
| Example 6 | 5 | 0.18 | 5 | 0.27 | 5 | 0.20 | 5 | 0.32 |
| Example 7 | 4 | 1.22 | 4 | 1.29 | 4 | 1.31 | 3 | 2.05 |
| Example 8 | 5 | 0.26 | 5 | 0.37 | 5 | 0.22 | 5 | 0.33 |
| Example 9 | 5 | 0.18 | 5 | 0.31 | 4 | 1.04 | 4 | 1.29 |
| Example 10 | 5 | 0.23 | 5 | 0.28 | 5 | 0.22 | 5 | 0.30 |
| Example 11 | 5 | 0.35 | 5 | 0.44 | 5 | 0.36 | 5 | 0.42 |
| Example 12 | 5 | 0.31 | 5 | 0.40 | 5 | 0.33 | 5 | 0.37 |
| Example 13 | 5 | 0.30 | 4 | 0.89 | 5 | 0.41 | 4 | 1.06 |
| Example 14 | 5 | 0.35 | 5 | 0.45 | 5 | 0.31 | 5 | 0.42 |
| Example 15 | 5 | 0.27 | 5 | 0.33 | 5 | 0.55 | 5 | 0.60 |
| Example 16 | 5 | 0.20 | 5 | 0.26 | 5 | 0.22 | 5 | 0.33 |
| Example 17 | 5 | 0.17 | 5 | 0.27 | 5 | 0.24 | 5 | 0.32 |
| Example 18 | 5 | 0.23 | 5 | 0.35 | 5 | 0.28 | 5 | 0.47 |
| Example 19 | 5 | 0.16 | 5 | 0.21 | 5 | 0.22 | 5 | 0.27 |
| Example 20 | 4 | 1.31 | 4 | 1.40 | 4 | 1.34 | 4 | 1.49 |
| Example 21 | 5 | 0.24 | 5 | 0.33 | 5 | 0.22 | 5 | 0.36 |

TABLE 6-continued

| | B system (red-yellow) color tone adaptability | | | | | | | |
|---|---|---|---|---|---|---|---|---|
| | Low chroma | | | | High chroma | | | |
| | 1 mm | | 5 mm | | 1 mm | | 5 mm | |
| | Evaluation by visual inspection | ΔE* | Evaluation by visual inspection | ΔE* | Evaluation by visual inspection | ΔE* | Evaluation by visual inspection | ΔE* |
| Example 22 | 5 | 0.23 | 5 | 0.37 | 5 | 0.31 | 5 | 0.38 |
| Example 23 | 5 | 0.24 | 5 | 0.34 | 5 | 0.26 | 5 | 0.41 |
| Example 24 | 5 | 0.26 | 5 | 0.21 | 5 | 0.27 | 5 | 0.42 |
| Example 25 | 5 | 0.35 | 5 | 0.38 | 5 | 0.33 | 4 | 0.96 |
| Example 26 | 5 | 0.24 | 5 | 0.31 | 5 | 0.21 | 5 | 0.29 |
| Example 27 | 5 | 0.17 | 5 | 0.22 | 5 | 0.13 | 5 | 0.28 |
| Example 28 | 5 | 0.17 | 5 | 0.28 | 5 | 0.20 | 5 | 0.33 |
| Example 29 | 5 | 0.22 | 5 | 0.24 | 5 | 0.25 | 5 | 0.30 |
| Comparative Example 1 | 1 | 4.66 | 1 | 5.23 | 1 | 4.85 | 1 | 5.41 |
| Comparative Example 2 | 1 | 4.82 | 1 | 5.11 | 1 | 4.74 | 1 | 5.36 |
| Comparative Example 3 | 2 | 3.95 | 1 | 4.98 | 2 | 3.67 | 1 | 4.76 |
| Comparative Example 4 | 1 | 4.70 | 1 | 5.02 | 1 | 4.81 | 1 | 5.44 |
| Comparative Example 5 | 1 | 4.87 | 1 | 5.22 | 1 | 4.78 | 1 | 5.62 |
| Comparative Example 6 | 2 | 3.74 | 1 | 4.53 | 2 | 3.68 | 1 | 4.55 |
| Comparative Example 7 | 2 | 3.89 | 2 | 3.92 | 1 | 4.60 | 1 | 4.65 |
| Comparative Example 8 | 1 | 4.60 | 1 | 5.97 | 1 | 4.79 | 1 | 6.10 |
| Comparative Example 9 | 1 | 8.01 | 1 | 7.73 | 1 | 6.74 | 1 | 7.01 |
| Comparative Example 10 | 2 | 3.94 | 1 | 4.55 | 1 | 4.67 | 1 | 5.28 |
| Comparative Example 11 | 1 | 4.75 | 3 | 3.45 | 2 | 4.00 | 2 | 4.17 |
| Comparative Example 12 | 3 | 3.38 | 1 | 4.64 | 2 | 3.98 | 1 | 6.07 |

As is understood from the results of Examples 1 to 29, it can be seen that when the conditions defined in the present invention are satisfied, a cured product of the curable composition exhibits a colored light on a black background and has satisfactory color tone adaptability, irrespective of the depth of the cavity.

As is understood from the results of Comparative Examples 1, 4, and 8, it can be seen that in a case in which a spherical filler having an average primary-particle diameter of less than 230 nm is used, the colored light is bluish, and the color tone adaptability to the tooth substance is inferior in a cavity formed over from the enamel to the dentine.

As is understood from the results of Comparative Examples 2, 3, 5, 6, 7, 10, 11, and 12, it can be seen that when the conditions defined in the present invention are not satisfied, the dental filling restorative material does not exhibit a colored light on a black background (Comparative Examples 2 and 5: the average particle diameter of the spherical filler was 80 nm, and the contrast ratio (Yb/Yw) did not satisfy 0.2 to 0.5; Comparative Examples 3 and 10: the shape of the filler was irregular); the colored light is weak (Comparative Example 6: the proportion of particles having a particle diameter in the range of ±5% based on the average primary-particle diameter of the spherical filler was 88%); a desired color tone is not obtained after filling, curing, and polishing (Comparative Example 7: nP<nF was not satisfied; Comparative Examples 11 and 12: the contrast ratio (Yb/Yw) did not satisfy 0.2 to 0.5), and the color tone adaptability is poor.

As is understood from the results of Comparative Example 9, with regard to a dental filling restorative material for which the color tone was adjusted to a color tone that matched A system of high-chroma hard resin teeth by adding pigments to the composition shown in Comparative Example 2, the spectral reflectance was measured on the black background color and the white background color using a color difference meter (manufactured by Tokyo Denshoku Co., Ltd., "TC-1800 MKII"), and it was observed that the spectral reflection characteristics corresponding to the pigments added are exhibits on both the black background color and the white background color. The color tone adaptability to a color tone that matched with A system of high-chroma hard resin teeth (corresponding to A4) was satisfactory; however, the color tone adaptability to other model teeth was low.

The disclosures of Japanese Patent Application No. 2017-082023 filed on Apr. 18, 2017, and Japanese Patent Application No. 2017-169730 filed on Sep. 4, 2017, are incorporated in their entirety in the present specification by reference.

The invention claimed is:

1. A curable composition comprising a polymerizable monomer (A); spherical particles (B) having an average primary-particle diameter in a range of 230 nm to 1,000 nm; a polymerization initiator (C), and inorganic particles (D) having an average primary-particle diameter of less than 100 nm, wherein 90% or more of individual particles constituting the spherical particles (B) lies in a range of ±5% based on the average primary-particle diameter, the polymerizable monomer (A) and the spherical particles (B) satisfy requirement (X1) represented by the following formula (1):

$$nP < nF \qquad (1)$$

in formula (1), nP represents a refractive index at 25° C. of a polymer obtained by polymerizing the polymerizable monomer (A); and nF represents a refractive index at 25° C. of the spherical particles (B), and when a 1 mm-thick cured product is formed from the curable composition and the Y value (Yb) of the colorimetric value according to the Munsell Color System of the colored light of the cured product on a black background and the Y value (Yw) of the colorimetric value according to the Munsell Color System of the colored light of the cured product on a white background are each measured using a color difference meter, the ratio therebetween, Yb/Yw, being within a range of 0.2 to 0.5.

2. The curable composition according to claim 1, wherein the average primary-particle diameter of the spherical particles (B) is in a range of 240 nm to 500 nm.

3. The curable composition according to claim 1, wherein the difference between the refractive index nF at 25° C. of the spherical particles (B) and the refractive index nP at 25° C. of a polymer of the polymerizable monomer (A) is 0.001 or more.

4. A dental restorative material consisting of the curable composition according to claim 1.

5. A curable composition comprising a polymerizable monomer (A); spherical particles (B) having an average primary-particle diameter in a range of 230 nm to 1,000 nm; a polymerization initiator (C), and inorganic particles (D) having an average primary-particle diameter of less than 100 nm, wherein 90% or more of individual particles constituting the spherical particles (B) lies in a range of ±5% based on the average primary-particle diameter, the polymerizable monomer (A) and the spherical particles (B) satisfy requirement (X1) represented by the following formula (1):

$$nP < nF \qquad (1)$$

in formula (1), nP represents a refractive index at 25° C. of a polymer obtained by polymerizing the polymerizable monomer (A); and nF represents a refractive index at 25° C. of the spherical particles (B), and when a 1 mm-thick cured product is formed from the curable composition and the Y value (Yb) of the colorimetric value according to the Munsell Color System of the colored light of the cured product on a black background and the Y value (Yw) of the colorimetric value according to the Munsell Color System of the colored light of the cured product on a white background are each measured using a color difference meter, the ratio therebetween, Yb/Yw, being within a range of 0.2 to 0.5, and when a cured product is formed from the curable composition, the cured product exhibits yellow to reddish colored light.

6. The curable composition according to claim 5, wherein the average primary-particle diameter of the spherical particles (B) is in a range of 240 nm to 500 nm.

7. The curable composition according to claim 5, wherein the difference between the refractive index nF at 25° C. of the spherical particles (B) and the refractive index nP at 25° C. of a polymer of the polymerizable monomer (A) is 0.001 or more.

8. A curable composition comprising a polymerizable monomer (A);

spherical particles (B) having an average primary-particle diameter in a range of 230 nm to 1,000 nm; and a polymerization initiator (C), wherein 90% or more of individual particles constituting the spherical particles (B) lies in a range of ±5% based on the average primary-particle diameter, the polymerizable monomer (A) and the spherical particles (B) satisfy requirement (X1) represented by the following formula (1):

$$nP < nF \qquad (1)$$

in formula (1), nP represents a refractive index at 25° C. of a polymer obtained by polymerizing the polymerizable monomer (A); and nF represents a refractive index at 25° C. of the spherical particles (B), when a 1 mm-thick cured product is formed from the curable composition and the Y value (Yb) of the colorimetric value according to the Munsell Color System of the colored light of the cured product on a black background and the Y value (Yw) of the colorimetric value according to the Munsell Color System of the colored light of the cured product on a white background are each measured using a color difference meter, the ratio therebetween, Yb/Yw, being within a range of 0.2 to 0.5, and wherein the 1 mm thick cured product has a maximum spectral reflectance at a wavelength of 607 nm to 757 nm as measured on a black background using a color difference meter.

9. The curable composition according to claim 8, wherein the average primary-particle diameter of the spherical particles (B) is in a range of 240 nm to 500 nm.

10. The curable composition according to claim 8, wherein the difference between the refractive index nF at 25° C. of the spherical particles (B) and the refractive index nP at 25° C. of a polymer of the polymerizable monomer (A) is 0.001 or more.

11. The curable composition according to claim 8, comprising inorganic particles (D) having an average primary-particle diameter of less than 100 nm.

* * * * *